(12) United States Patent
Gray et al.

(10) Patent No.: US 10,369,120 B2
(45) Date of Patent: Aug. 6, 2019

(54) T TYPE CALCIUM CHANNEL INHIBITORS

(71) Applicant: University of Virginia Patent Foundation, Charlottesville, VA (US)

(72) Inventors: Lloyd S. Gray, Louisa, VA (US); Timothy L. Macdonald, Charlottesville, VA (US); Doris M. Haverstick, Charlottesville, VA (US); Jaclyn R. Patterson, Conshohocken, PA (US); William F. McCalmont, Myersville, MD (US)

(73) Assignee: University of Virginia Patent Foundation, Charlottesville, VA (US)

(*) Notice: Subject to any disclaimer, the term of this patent is extended or adjusted under 35 U.S.C. 154(b) by 0 days.

(21) Appl. No.: 14/933,237

(22) Filed: Nov. 5, 2015

(65) Prior Publication Data

US 2016/0136115 A1 May 19, 2016

Related U.S. Application Data

(62) Division of application No. 11/660,693, filed as application No. PCT/US2005/029862 on Aug. 22, 2005, now Pat. No. 9,212,127.

(60) Provisional application No. 60/603,168, filed on Aug. 20, 2004.

(51) Int. Cl.
| | |
|---|---|
| *A61K 31/12* | (2006.01) |
| *A61K 31/14* | (2006.01) |
| *A61K 45/06* | (2006.01) |
| *A61K 31/085* | (2006.01) |
| *A61K 31/137* | (2006.01) |
| *A61K 31/138* | (2006.01) |
| *C07C 217/58* | (2006.01) |
| *C07C 217/60* | (2006.01) |
| *C07C 217/62* | (2006.01) |

(52) U.S. Cl.
CPC ............ *A61K 31/14* (2013.01); *A61K 31/085* (2013.01); *A61K 31/12* (2013.01); *A61K 31/137* (2013.01); *A61K 31/138* (2013.01); *A61K 45/06* (2013.01); *C07C 217/58* (2013.01); *C07C 217/60* (2013.01); *C07C 217/62* (2013.01)

(58) Field of Classification Search
None
See application file for complete search history.

(56) References Cited

U.S. PATENT DOCUMENTS

| 3,666,811 A | 5/1972 | van der Stelt |
| 5,171,752 A | 12/1992 | Caldirola et al. |
| 5,919,816 A | 7/1999 | Hausheer et al. |
| 6,372,719 B1 | 4/2002 | Cunningham |
| 9,212,127 B2 | 12/2015 | Gray et al. |
| 9,427,429 B2 * | 8/2016 | Gray .................. A61K 31/4015 |
| 2001/0049447 A1 * | 12/2001 | Li ........................ C07D 235/14 548/309.7 |
| 2009/0234019 A1 | 9/2009 | Gray et al. |

FOREIGN PATENT DOCUMENTS

| AU | 2005277156 B2 | 3/2012 |
| EP | 1778619 B1 | 4/2012 |
| FR | 2355833 A1 | 1/1978 |
| JP | 52156871 | 12/1977 |
| JP | 4927735 B2 | 2/2012 |
| WO | WO-9640097 A1 | 12/1996 |
| WO | WO-2005077082 A2 | 8/2005 |

(Continued)

OTHER PUBLICATIONS

Hiraga et al. "The Bisphosphonate Ibandronate Promotes Apoptosis in MDA-MB-231 Human Breast Cancer Cells in Bone Metastases". Cancer Research. Jun. 2001; 61:4418-4424.*

(Continued)

*Primary Examiner* — Leslie A. Royds Draper

(74) *Attorney, Agent, or Firm* — Schwegman Lundberg & Woessner, P.A.

(57) ABSTRACT

The present invention provides novel T type calcium channel inhibitors of formula (I), the use thereof in the treatment of a disease or condition in a mammal associated with influx of extracellular calcium via T type calcium channels, wherein $R_1$ is $C_1$-$C_4$ alkyl, hydroxy, or $C_1$-$C_4$ alkoxy; Z is NH, NCH$_3$, O, S, or CH$_2$; Y is NH, O, or CH$_2$ with the proviso that Y and Z are not the same; $R_2$ is H, halo, NH$_2$, $C_1$-$C_4$ alkyl, hydroxy, or $C_1$-$C_4$ alkoxy; m and n are independently selected from integers ranging from 1-5 with the proviso that m+n=an integer ranging from 2-9; and $R_3$ is H, halo, NH$_2$, $C_1$-$C_4$ alkyl, hydroxy, or $C_1$-$C_4$ alkoxy.

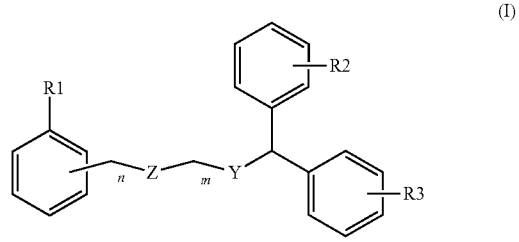

(I)

3 Claims, 8 Drawing Sheets
Specification includes a Sequence Listing.

(56) References Cited

FOREIGN PATENT DOCUMENTS

WO   WO-2006023883 A2   3/2006
WO   WO-2006023883 A3   3/2006

OTHER PUBLICATIONS

Kansal et al. "Possible Antihypertensive Agents: Syntheses of N-Aralkyl-beta-substituted Phenylethylamines & N-Alkyl/acyl-6,7-dimethoxy-1-[(alpha-phenyl-beta-substituted phenyl) ethyl]-1,2,3,4-Tetrahydroisoquinolines". Indian Journal of Chemistry, 1981; 20B :885-890.*
Silverman RB. "The Organic Chemistry of Drug Design and Drug Action" (Second Edition). Northwestern University (Department of Chemistry), Section 2, p. 29-32, 2004.*
STN Registry No. 848993-55-5. STN Database, (Apr. 22, 2005), 1 pg.
STN Registry No. 849029-40-9. STN Database, (Apr. 22, 2005), 1 pg.
STN Registry No. 849826-06-8. STN Database, (May 5, 2005), 1 pg.
"U.S. Appl. No. 11/660,693, Final Office Action dated Nov. 25, 2011", 11 pgs.
"U.S. Appl. No. 11/660,693, Non Final Office Action dated Apr. 16, 2015", 12 pgs.
"U.S. Appl. No. 11/660,693, Non Final Office Action dated Jul. 11, 2014", 17 pgs.
"U.S. Appl. No. 11/660,693, Non Final Office Action dated Sep. 13, 2011", 12 pgs.
"U.S. Appl. No. 11/660,693, Notice of Allowance dated Aug. 5, 2015", 8 pgs.
"U.S. Appl. No. 11/660,693, Preliminary Amendment filed Feb. 20, 2007", 3 pgs.
"U.S. Appl. No. 11/660,693, Preliminary Amendment filed Nov. 18, 2008", 3 pgs.
"U.S. Appl. No. 11/660,693, Response filed Jan. 5, 2012 to Final Office Action dated Nov. 25, 2011", 9 pgs.
"U.S. Appl. No. 11/660,693, Response filed Apr. 8, 2015 to Final Office Action dated Dec. 23, 2014", 15 pgs.
"U.S. Appl. No. 11/660,693, Response filed May 20, 2015 to Non Final Office Action dated Apr. 16, 2015", 7 pgs.
"U.S. Appl. No. 11/660,693, Response filed Oct. 13, 2011 to Non Final Office Action dated Sep. 13, 2011".
"U.S. Appl. No. 11/660,693, Response filed Oct. 23, 2014 to Non Final Office Action dated Jul. 11, 2014", 15 pgs.
"U.S. Appl. No. 11/660,693, Response filed Aug. 10, 2011 to Restriction Requirement dated Jun. 10, 2011", 8 pgs.
"U.S. Appl. No. 11/660,693, Restriction Requirement dated Jun. 10, 2011", 10 pgs.
"U.S. Appl. No. 14/147,858, Final Office Action dated Dec. 23, 2014", 15 pgs.
"Australian Application Serial No. 2005277156, First Examiner Report dated Aug. 10, 2010", 3 Pgs.
"Australian Application Serial No. 2005277156, Office Action Response filed Nov. 8, 2011", 11 pgs.
"Canadian Application Serial No. 2,576,191, Non Final Office Action dated Mar. 19, 2012", 2 pgs.
"Canadian Application Serial No. 2,576,191, Response filed Jan. 18, 2012 to Office Action dated Nov. 24, 2011", 16 pgs.
"Canadian Application Serial No. 2,576,191, Response filed Apr. 26, 2012 to Office Action dated Mar. 19, 2012", 4 pgs.
"Canadian Application Serial No. 2,576191, Office Action dated Nov. 24, 2011", 4 pgs.
"European Application Serial No. 05791569.6, Extended European Search Report dated Mar. 28, 2008", 17 pgs.
"European Application Serial No. 05791569.6, Office action dated Feb. 24, 2010", 3 pgs.
"European Application Serial No. 05791569.6, Office Action dated Jul. 23, 2009", 5 pgs.
"European Application Serial No. 05791569.6, Office Action dated Oct. 21, 2008", 2 pgs.
"European Application Serial No. 05791569.6, Response filed Jan. 20, 2010 to Office Action dated Jul. 23, 2009", 20 pgs.
"European Application Serial No. 05791569.6, Response filed Apr. 30, 2009 to Office Action dated Oct. 21, 2008", 21 pgs.
"European Application Serial No. 05791569.6, Response filed Jul. 1, 2010 to Office action dated Feb. 24, 2010", 11 pgs.
"International Application Serial No. PCT/US2005/029862, International Search Report and Written Opinion dated Jun. 8, 2006", 6 pgs.
"International Application Serial No. PCT/US2005/029862, Written Opinion dated Jun. 6, 2006", 5 pgs.
"Japanese Application Serial No. 2007-528094, Response filed Nov. 9, 2011 to Office Action dated May 10, 2011", 9 pgs.
"Japanese Application Serial No. 2007-528094, Office Action dated May 10, 2011", 4 pgs.
"N-[(4-methoxyphenyl)methyl]-4-(1-methylethoxy)-gamma-(4-methylphenyl)-benzenepropanamine", STN Registry No. 384361-15-3. STN Database., (Jan. 19, 2002), 1 pg.
"N-[(4-methoxyphenyl)methyl]-4-(1-methylethoxy)-gamma-phenyl-benzenepropanamine", STN Registry No. 384360-90-1. STN Database, (Jan. 19, 2002), 1 pg.
"Products and Services", Interbioscreen Ltd., [Online]. Retrieved from the Internet: https://web.archive.org/web/20020410012735/ http://ibscreen.com/products.shtml, (Apr. 10, 2002), 2 pgs.
Berridge, M.J., et al., "The Versatility and Universality of Calcium Signalling", Nature Reviews-Molecular Cell Biology 1, (2000), 11-21.
Brooks, G., et al., "Over-Expression of the Voltage-Gated T-Type Calcium Channel Induces Vascular Smooth Muscle Cell Proliferation", Circulation, 100, I-209.
Cahalan, M. D., et al., "Molecular Properties and Physiological Roles of Ion Channels in the Immune System", Journal of Clinical Immunology, 21(4), (2001), 235-252.
Chemin, J., et al., "Specific Contribution of Human T-Type Calcium Channel Isotypes (a1G, a1H and a1I) to Neronal Excitability", Journal of Physiology, 540, 1, (2002), 3-14.
Clapham, David E., "Sorting Out MIC, TRP, and CRAC Ion Channels", Journal of General Physiology, 120, (2002), 217-220.
Clozel, J. P., et al., "Voltage Gated T-Type Ca2+ Channels and Heart Failure", Proceedings of the Association of American Physicians, 111(5), (1999), 429-437.
Densmore, J. J., et al., "A Voltage-Gated Calcium Channel is Linked to the Antigen Receptor in Jurkat T Lymphocytes", FEBS Letter, 312(2,3), (1992), 161-164.
Densmore, J. J., et al., "A Voltage-Operable Current is Involved in Ca2+ Entry in Human Lymphocytes whereas Icrac has no Apparent Role", American Physiological Society, 271, (1996), C1494-C1503.
Dogrul, A., et al., "Reversal of experimental neuropathic pain by T-type calcium channel blockers", Pain, 105(1-2), (Sep. 2003), 159-68.
Falch, E., et al., "GABA uptake inhibitors containing mono- and diarylmethoxyalkyl N-substituents", Drug Des Deliv.. 4(3), (May 1989), 205-15.
Falch, E., et al., "GABA uptake inhibitors containing mono- and diarylmethoxyalkyl N-substituents", Drug Des Deliv., 4(3), (May 1989), 205-215.
Harper, J. V., et al., "Functional T-Type Calcium Channels are Necessary for G1-S Progression in Vascular Smooth Muscle Cells", Circulation, 102(18), II-48.
Haverstick, D. M., et al., "Calmodulin Regulation of Ca2+ Entry in Jurkat T Cells", Cell Calcium, 23(6), (1998), 361-367.
Haverstick, D. M., et al., "Increased Intracellular Ca2+ Induces Ca2+ Influx in Human T Lymphocytes", Molecular Biology of the Cell, 4, (1993), 173-184.
Haverstick, D. M, et al., "Inhibition of human prostate cancer proliferation in vitro and in a mouse model by a compound synthesized to block Ca2+ entry", Cancer Res., 60(4), (Feb. 15, 2000), 1002-8.
Jones, G., et al., "Cancer Therapy: Phenothiazines in an Unexpected Role", Tumori, 71, (1985), 563-569.

(56) References Cited

OTHER PUBLICATIONS

Kansal, V. K., et al., "Possible Antihypertensive Agents: Syntheses of N-Aralkyl-b-substituted Phenylethylamines & N-Alkyl/acyl-6, 7-dimethoxY-I-['(a-phenyl-b-substituted phenyl) ethyl]-I, 2,3 ,4-tetrahydroisoquinolines", Indian Journal of Chemistry, vol. 20B, (1982), 885-890.

Kansal, V. K., et al., "Possible Antihypertensive Agents: Syntheses of N-Aralkyl-beta betasubstituted Phenylethylamines & N-AlkyVacyl-6, 7-dimethoxy-i [(alpha-phenyl-beta[(alpha-phenyl-betasubstituted phenyl) ethyl]-1,2,3,4-tetrahydroisoquinolines", Indian Journal of Chemistry, vol. 20B, (1981), 885-890.

Lee, G., et al., "Randomized comparison of T-type versus L-type calcium-channel blockade on exercise duration in stable angina: Results of the Posicor Reduction of Ischemia During Exercise (PRIDE) trial", American Heart Journal, 144(1), (2002), 60-67.

Lee, J-H, et al., "Nickel Block of Three Cloned T-Type Calcium Channels: Low Concentrations Selectively Block a1H", Biophysical Journal, 77, (1999), 3034-3042.

Mariot, P., et al., "Overexpression of an alpha 1H (Cav3.2) T-type calcium channel during neuroendocrine differentiation of human prostate cancer cells.", The Journal of Biological Chemistry 227(13), (2002), 10824-10833.

Massie, B. M, et al., "Mibefradil: a selective T-type calcium antagonist", Am J Cardiol., 80(9A), (Nov. 6, 1997), 23I-32I.

McCalmont, W. F, et al., "Design, synthesis, and biological evaluation of novel T-Type calcium channel antagonists", Bioorg Med Chem Lett., 14(14), (Jul. 16, 2004), 3691-5.

McCalmont, W. F, et al., "Investigation into the structure-activity relationship of novel concentration dependent, dual action T-type calcium channel agonists/antagonists", Bioorg Med Chem., 13(11), (Jun. 1, 2005), 3821-3839.

McDonald, T. F., et al., "Regulation and Modulation of Calcium Channels in Cardiac, Skeletal, and Smooth Muscle Cells", Physiological Reviews, 74(2), (1994), 365-507.

Merritt, J. E., et al., "Regulation of Cytosolic Free Calcium in Fura-2 Loaded Rat Parotid Acinar Cells", The Journal of Biological Chemistry, 262(36), (1987), 17362-17369.

Merritt, J. E., et al., "Use of Manganese to Discriminate Between Calcium Influx and Mobilization from Internal Stores in Stimulated Human Neutrophils", The Journal of Biological Chemistry, 264(3), (1989), 1522-1527.

Monteil, A., et al., "Molecular and Functional Properties of the Human a1G Subunit that Forms T-Type Calcium Channels", The Journal of Biological Chemistry, 275(9), (2000), 6090-6100.

Neher, E., et al., "The Patch Clamp Technique", Scientific American, (1992), 44-51.

Patani, G. A, et al., "Bioisosterism: A Rational Approach in Drug Design", Chem Rev., 96(8), (Dec. 19, 1996), 3147-3176.

Putney, J. W., et al., "Capacitative Calcium Entry Channels", BioEssays, 21, (1999), 38-46.

Skryma, R., et al., "Store Depletion and Store-Operated Ca2+ Current in Human Prostate Cancer LNCaP Cells: Involvement in Apoptosis", Journal of Physiology, 527, Pt. 1, (2000), 71-83.

Talley, E. M, et al., "Low-voltage-activated calcium channel subunit expression in a genetic model of absence epilepsy in the rat", Brain Res Mol Brain Res., 75(1), (Jan. 10, 2000), 159-65.

* cited by examiner

Jurkat forward alignment

```
1     ctcttgggggtaggcatgggcgtggcagctgtgcacatgatgaggggaggggacaggctg  60
      ||||||||||||||||||||||||||||||||||||||||||||||||||||||||||||
3348  ctcttgggggtaggcatgggcgtggcagctgtgcacatgatgaggggaggggacaggctg  3289

61    cctcgtcctccaggtgcccgttgggggtcacggccagggaaacacatcttcagctctgt  120
      |||||||||||||||||||||||||||||||||||||||| |||||||||||||||||||
3288  cctcgtcctccaggtgcccgttgggggtcacggccaggg-aacacatcttcagctctgt  3230

121   ggtctggagttctctgagcttgtggaagtcctcctcgaag  160
      ||||||||||||||||||||||||||||||||||||||||
3229  ggtctggagttctctgagcttgtggaagtcctcctcgaag  3190
```

SK-N-SH forward alignment

```
21    caggtgcgtgtggtcggtgggtggtccgggttctggcgggtggagtacgctgggctggcc  80
      ||||||||||||||||||||||||||||||||||||||||||||||||||||||||||||
3507  caggtgcgtgtggtcggtgggtggtccgggttctggcgggtggagtacgctgggctggcc  3566

81    gggcagggcccccataaggcaatccctaggttgggggattcctggtcctgggagcctggc  140
      ||||||||||||||||||||||||||||||||||||||||||||||||||||||||||||
3567  gggcagggcccccataaggcaatccctaggttgggggattcctggtcctgggagcctggc  3626

141   agctctaggggcccattcctccctctgtcccgcagagctnaagatgtgttccctggccgt  200
      ||||||||||||||||||||||||||||||||||||||| ||||||||||||||||||||
3627  agctctaggggcccattcctccctctgtcccgcagagctgaagatgtgttccctggccgt  3686

201   naccccaacgggcacctggagggacnaggcagcctgtcccntccntnatnatgtgcac  260
      |||||||||||||||||||||||||  |||||||||||||| |||| | || ||||||||
3687  gaccccaacgggcacctggagggacgaggcagcctgtcccctccctcatcatgtgcac  3746

261   agntgccacgccatgcntaccccaanagctcaccnttcntgg  304
      || ||||||||||||||| |||||||| ||||||||| ||| |||
3747  agctgccacgccatgcctaccccaagagctcaccattcctgg  3790
```

FIG. 4

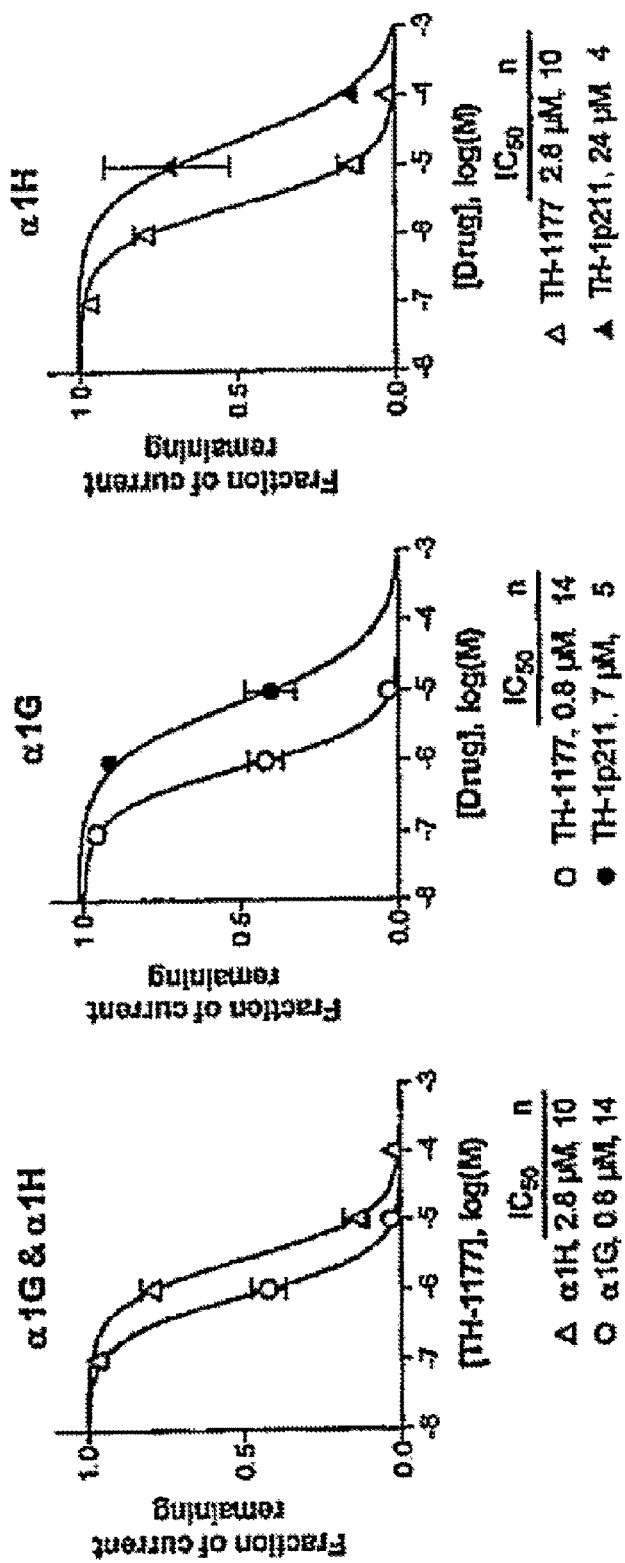

SEQUENCE LISTING

```
<160> NUMBER OF SEQ ID NOS: 4

<210> SEQ ID NO 1
<211> LENGTH: 160
<212> TYPE: DNA
<213> ORGANISM: Artificial Sequence
<220> FEATURE:
<223> OTHER INFORMATION: A synthetic PCR primer (forward)

<400> SEQUENCE: 1
ctcttggggg taggcatggg cgtggcagct gtgcacatga tgaggggagg ggacaggctg      60
cctcgtccct ccaggtgccc gttgggggtc acggccaggg aaacacatct tcagctctgt     120
ggtctggagt tctctgagct tgtggaagtc ctcctcgaag                            160

<210> SEQ ID NO 2
<211> LENGTH: 160
<212> TYPE: DNA
<213> ORGANISM: Artificial Sequence
<220> FEATURE:
<223> OTHER INFORMATION: A synthetic PCR primer (reverse)

<400> SEQUENCE: 2
ctcttggggg taggcatggg cgtggcagct gtgcacatga tgaggggagg ggacaggctg      60
cctcgtccct ccaggtgccc gttgggggtc acggccaggg aaacacatct tcagctctgt     120
ggtctggagt tctctgagct tgtggaagtc ctcctcgaag                            160

<210> SEQ ID NO 3
<211> LENGTH: 284
<212> TYPE: DNA
<213> ORGANISM: Artificial Sequence
<220> FEATURE:
<223> OTHER INFORMATION: A synthetic PCR primer (forward)
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (222)..(222)
```

```
<223> OTHER INFORMATION: n is a, c, g, or t
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (229)..(229)
<223> OTHER INFORMATION: n is a, c, g, or t
<220> FEATURE:
<221> NAME/KEY: misc_feature
<222> LOCATION: (232)..(232)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (268)..(268)
<223> OTHER INFORMATION: n is a, c, g, or t
<220> FEATURE:
<221> NAME/KEY: misc_feature
<222> LOCATION: (277)..(277)
<223> OTHER INFORMATION: n is a, c, g, or t
<220> FEATURE:
<221> NAME/KEY: misc_feature
<222> LOCATION: (281)..(281)
<223> OTHER INFORMATION: n is a, c, g, or t

<400> SEQUENCE: 3
caggtgcgtg tggtcggtgg gtggtccggg ttctggcggg tggagtacgc tgggctggcc      60
gggcagggcc cccataaggc aatccctagg ttgggggatt cctggtcctg ggagcctggc     120
agctctaggg gcccattcct ccctctgtcc cgcagagctn aagatgtgtt ccctggccgt     180 naccccaac gggcacctgg agggacnagg cagcctgtcc cntcccntna tnatgtgcac     240
agntgccacg cccatgcnta cccccaanag ctcaccnttc ntgg                      284

<210> SEQ ID NO 4
<211> LENGTH: 284
<212> TYPE: DNA
<213> ORGANISM: Artificial Sequence
<220> FEATURE:
<223> OTHER INFORMATION: A synthetic PCR primer (reverse)

<400> SEQUENCE: 4
caggtgcgtg tggtcggtgg gtggtccggg ttctggcggg tggagtacgc tgggctggcc      60
gggcagggcc cccataaggc aatccctagg ttgggggatt cctggtcctg ggagcctggc     120
agctctaggg gcccattcct ccctctgtcc cgcagagctg aagatgtgtt ccctggccgt     180 gaccccaac gggcacctgg agggacgagg cagcctgtcc cctcccctca tcatgtgcac     240
agctgccacg cccatgccta cccccaagag ctcaccattc ctgg                      284
```

T TYPE CALCIUM CHANNEL INHIBITORS

CROSS REFERENCE TO RELATED APPLICATION

This application is a divisional of U.S. patent application Ser. No. 11/660,693, filed Nov. 18, 2008, which is a U.S. National Stage Filing under 35 U.S.C. 371 from International Application No. PCT/US2005/029862, filed on Aug. 22, 2005, which claims the benefit of priority to U.S. Provisional Application No. 60/603,168, filed Aug. 20, 2004, all of which are incorporated herein by reference in their entireties.

BACKGROUND OF THE INVENTION

Influx of extracellular calcium is critical for a number of vital cellular processes. Calcium influx is generally mediated by calcium channels, which are grouped into several families one of which is the T type calcium channel family. Pharmacological modulation of the T type calcium channel's function is tremendously important in the practice of medicine; for example, T type calcium channel inhibitors are in widespread use in the treatment of neurological diseases (e.g. epilepsy, petit mal seizure, absence seizure, neuropathic pain, and etc.) and cardiovascular diseases (e.g. hypertension, unstable angina, and etc.). For example, mibefradil, a T type calcium inhibitor, was clinically efficacious in treating hypertension and cardiac arrhythmia. Studies also suggest that T-type calcium channels may play an important role in age related macular degeneration. Recently, we have showed that the α1H and δ 25 isoforms of T type calcium channels are present in cancer cell lines and that novel chemical agents could be synthesized to block calcium entry via this channel thus inhibiting cancer cell proliferation.

Ca2+ entry is critical for cellular proliferation. Because unusually rapid proliferation is a hallmark of cancer, elucidation of the mechanism of Ca2+ entry is of scientific importance with potential clinical significance. However, the mechanism or mechanisms of Ca2+ entry in electrically non-excitable cells, which constitute most types of cancer, remain elusive. The majority of cancers arise from cell types considered "electrically non-excitable." This is to distinguish the means of regulation of Ca2+ entry in these cells from those having action potentials, that is "electrically excitable" cells. In electrically excitable cells, an action potential opens voltage gated Ca2+ channels that admit the Ca2+ required for initiating events such as neurosecretion. In electrically non-excitable cells, the regulatory mechanism activating Ca2+ entry is unclear in part because of the uncertainty about the molecular mechanism by which Ca2+ entry occurs.

The two types of ion channels or transporters most commonly implicated in capacitative Ca+ entry are $I_{CRAC}$ and members of the Trp. These two channel types do not share many properties other than relative selectivity for Ca2+, albeit sometimes very weak, and lack of voltage dependent gating. It has been difficult, however, to tie these proteins' function to capacitative Ca+ entry. This may reflect a particular complexity of Ca2+ signaling in electrically non-excitable cells arising from participation of numerous channels and transporters in this process. It is also possible that the primary means of Ca2+ entry in electrically non-excitable cells has yet to be fully elucidated.

We have taken an alternative approach to dissecting the Ca2+ entry pathway in electrically non-excitable cells. We first took advantage of Ca+ entry blockade by Ni2+, as measured by fluorescence techniques (Merritt, J. E. and Rink, T. J. 1987. Regulation of cytosolic free calcium in fura-2-loaded rat parotid.acinar cells. J. Biol. Chem. 262: 17362-17369; Merritt, J. E., Jacob, R., and Hallam, T. J. 1989. Use of manganese to discriminate between calcium influx and mobilization from internal stores in stimulated human neutrophils. J. Biol. Chem. 264:1522-1527; Skryma, R., Mariot, P., Bourhis, X. L., Coppenolle, F. V., Shuba, Y., Abeele, F. V., Legrand, G., Humez, S., Boilly, B., and Prevarskaya, N. 2000. Store depletion and store-operated $Ca^{2+}$ current in human prostate cancer LNCaP cells: involvement in apoptosis. J. Physiol. (Lond.) 527 Pt 1:71-83), to identify compounds in the published literature with a similar ability. The structure/activity relationship of these known compounds was used to guide the synthesis of novel compounds with enhanced potency to block Ca2+ entry into and proliferation of several cancer cell lines. Administration of one of these compounds, TH-1177, significantly extended the lifespan of nude mice inoculated with human PC3 prostate cancer cells (Haverstick, D. M., Heady, T. N., Macdonald, T. L., and Gray, L. S. 2000. Inhibition of human prostate cancer proliferation in vitro and in a mouse model by a compound synthesized to block $Ca^{2+}$ entry. Cancer Res 60:1002-1008). We show here that two representative compounds block the Ca2+ current through the heterologously expressed α1H isoform of T type Ca2+ channels and inhibit proliferation of HEK293 cells stably transfected with this isoform. These two compounds blocked the Ca2+ current and capacitative Ca2+ entry with similar potencies and identical stereoselectivity. Importantly, cell lines sensitive to our novel compounds express message for α1H, its δ 25 splice variant, or both while a cell line resistant to our compounds does not detectably express either message.

The library of compounds we have developed has apparently broad activity against cancer cell lines from various tissues. They act cytostatically and are equally potent at inhibiting hormone sensitive and insensitive breast and prostate cancer lines. We demonstrate here the likely target of their anti-proliferative activity. Taken together, these observations raise the possibility of directed chemical synthesis of compounds that inhibit Ca2+ entry into and thereby proliferation of cancer cells.

SUMMARY OF THE INVENTION

Accordingly, the present invention provides a method for the treatment of a disease or condition in a mammal associated with influx of extracellular calcium via T type calcium channels, which comprises administering to the mammal a therapeutically effective amount of a T type calcium channel inhibitor, a prodrug thereof, or a pharmaceutically acceptable salt of said inhibitor or prodrug. Preferably, the T type calcium channel inhibitor has a structure represented by Formula (I):

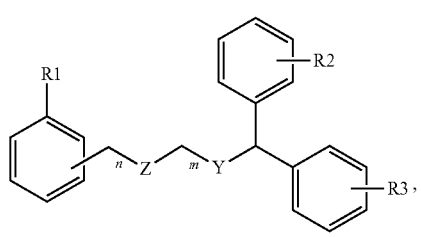

Formula(I)

wherein
R$_1$ is C$_1$-C$_4$ alkyl, hydroxy, or C$_1$-C$_4$ alkoxy;
Z is NH, NCH$_3$, O, S, or CH$_2$;
Y is NH, O, or CH$_2$ with the proviso that Y and Z are not the same;
R$_2$ is H, halo, NH$_2$, C$_1$-C$_4$ alkyl, hydroxy, or C$_1$-C$_4$ alkoxy;
m and n are independently selected from integers ranging from 1-5 with the proviso that m+n=an integer ranging from 2-9; and
R$_3$ is H, halo, NH$_2$, C$_1$-C$_4$ alkyl, hydroxy, or C$_1$-C$_4$ alkoxy.
More preferably, R$_1$ is hydroxy or C$_1$-C$_4$ alkoxy; Z is N or O; R$_2$ is H, halo, NH$_2$ or hydroxy; and R$_3$ is H. The disease or condition is preferably selected from the group consisting of unstable angina, hypertension, epilepsy, neuropathic pain, petit mal seizure, absence seizure, age related macular degeneration, cancer, and pre-cancerous condition.

The present invention also provides a method for reducing proliferation of electrically non-excitable cells, which comprises administering a T type calcium channel inhibitor of formula (I) as described above.

In another aspect, the present invention provides a compound of Formula (I)

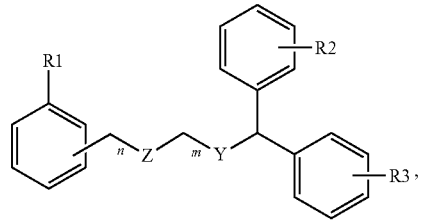

Formula(I)

wherein
R$_1$ is C$_1$-C$_4$ alkyl, hydroxy, or C$_4$-C$_4$ alkoxy;
Z is NH, NCH$_3$, O, S, or CH$_2$;
Y is NH, O, or CH$_2$ with the proviso that Y and Z are not the same;
R$_2$ is H, halo, NH$_2$, C$_1$-C$_4$ alkyl, hydroxy, or C$_4$-C$_4$ alkoxy;
m and n are independently selected from integers ranging from 1-5 with the proviso that m+n=an integer ranging from 2-9; and
R$_3$ is H, halo, NH$_2$, C$_1$-C$_4$ alkyl, hydroxy, or C$_1$-C$_4$ alkoxy;
or a pharmaceutically acceptable salt thereof.
Preferably, R$_1$ is hydroxy or C$_1$-C$_4$ alkoxy; Z is N or O; R$_2$ is H, halo, NH$_2$ or hydroxy; and R$_3$ is H. More preferably, the compound of formula (I) is selected from the group consisting of the following compounds:

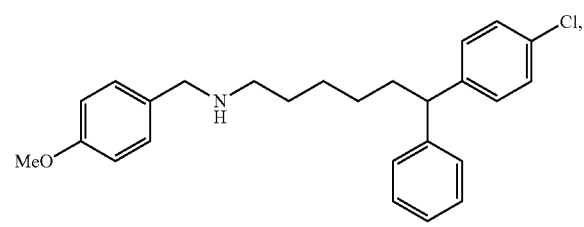

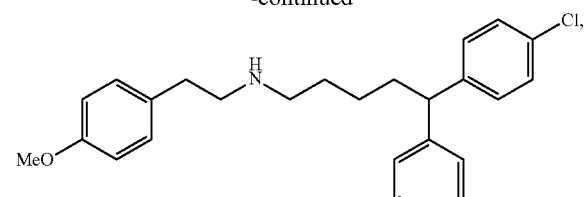

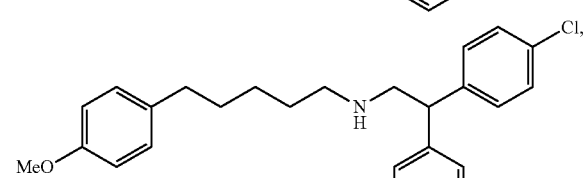

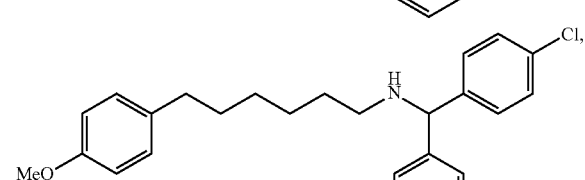

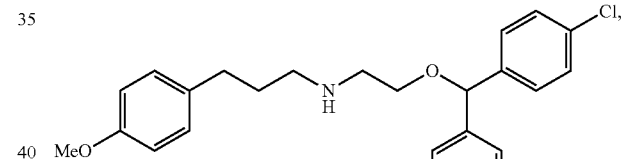

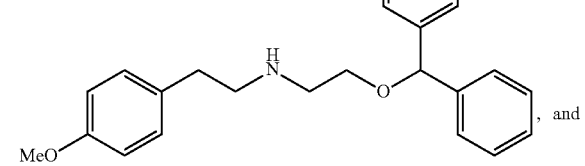, and

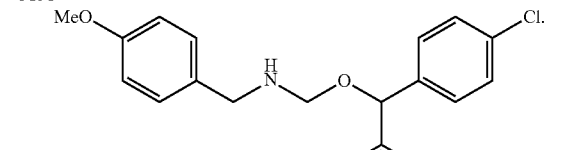

In another aspect, the present invention provides a pharmaceutical composition comprising a therapeutically effective amount of a compound of formula (I) as described above, a prodrug of said compound or a pharmaceutically acceptable salt of said compound or prodrug and a pharmaceutically acceptable carrier, vehicle or diluent.

In another aspect, the present invention provides a method for the treatment of cancer or pre-cancerous condition in a mammal, which comprises administering to the mammal a therapeutically effective amount of a compound of formula (I) as described above, a prodrug thereof, or a pharmaceutically acceptable salt of said compound or prodrug in combination with one or more anti-tumor agent.

The present application also provides pharmaceutical combination composition comprising a therapeutically effective amount of a combination of a compound of formula (I) as described above, a prodrug thereof, or a pharmaceutically acceptable salt of said compound or prodrug; and one or more anti-tumor agent.

BRIEF DESCRIPTION OF THE DRAWINGS

FIG. 4. The sequences of the amplicons shown in FIG. 4 (SEQ ID NOS: 1-4) are virtually identical to either α1H or its δ 25 splice variant. The amplicons shown in FIG. 4 were sequenced as described in Materials and Methods. The GenBank database was then queried and the alignments shown were obtained.

DEFINITIONS

Figure 1A:
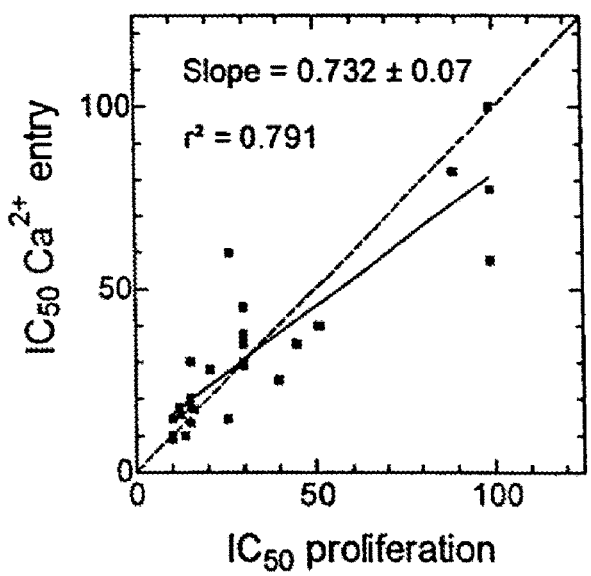
FIG. 1. Identification of known compounds that block Ca2+ entry and proliferation and design of novel compounds with increased potency. Proliferation and Ca2+ entry were determined in Jurkat cancer cells as described below in the Materials and Methods. Individual concentration-response curves for each activity and compound were constructed and IC50 values were calculated. The calculated least squares regression in shown as a solid line and a line with a slope of one in shown as a dashed line. Panel A: Using Ni2+ sensitivity as a guide, known compounds were identified that block Ca2+ entry and proliferation in Jurkat cells. Panel B: An SAR was developed from the data depicted in panel A leading to the synthesis of novel compounds that block Ca2+ entry and proliferation Jurkat cells.

In describing and claiming the invention, the following terminology will be used in accordance with the definitions set forth below.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

As used herein, the term "treating", "treat" or "treatment" includes administering therapy to prevent, cure, or alleviate/prevent the symptoms associated with, a specific disorder, disease, injury or condition. For example treating cancer includes inhibition or complete growth arrest of a tumor, reduction in the number of tumor cells, reduction in tumor size, inhibition of tumor cell infiltration into peripheral organs/tissues, inhibition of metastasis as well as relief, to some extent, of one or more symptoms associated with the disorder. The treatment of cancer also includes the administration of a therapeutic agent that directly decreases the pathology of tumor cells, or renders the tumor cells more susceptible to treatment by other therapeutic agents, e.g., radiation and/or chemotherapy. As used herein, the term "treating" includes prophylaxis of the specific disorder or condition, or alleviation of the symptoms associated with a specific disorder or condition and/or preventing or eliminating said symptoms.

As used herein, the term "pharmaceutically acceptable carrier, vehicle or diluent" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the U.S. Federal government or listed in the U.S. Pharmacopeia for use in animals, including humans.

The term "therapeutically effective amount" means an amount of a compound of the present invention that ameliorates, attenuates or eliminates a particular disease or condition or prevents or delays the onset of a particular disease or condition.

By "mammal" it is meant to refer to all mammals, including, for example, primates such as humans and monkeys. Examples of other mammals included herein are rabbits, dogs, cats, cattle, goats, sheep and horses. Preferably, the mammal is a female or male human.

The phrase "compound(s) of the present invention" or "compound(s) of Formula (I)" or the like, shall at all times be understood to include all active forms of such compounds, including, for example, the free form thereof, e.g., the free acid or base form, and also, all prodrugs, polymorphs, hydrates, solvates, tautomers, and the like, and all pharmaceutically acceptable salts, unless specifically stated otherwise. It will also be appreciated that suitable active metabolites of such compounds are within the scope of the present invention.

The expression "prodrug" refers to compounds that are drug precursors which following administration, release the drug in vivo via some chemical or physiological process (e.g., a prodrug on being brought to the physiological pH or through enzyme action is converted to the desired drug form).

The expression "pre-cancerous condition" refers to a growth that is not malignant but is likely to become so if not treated. A "pre-cancerous condition" is also known as "pre-malignant condition" by one of ordinary skill in the art.

As used herein the term "anti-tumor agent" relates to agents known in the art that have been demonstrated to have utility for treating neoplastic disease. For example, antitumor agents include, but are not limited to, antibodies, toxins, chemotherapeutics, enzymes, cytokines, radionuclides, photodynamic agents, and angiogenesis inhibitors. Toxins include ricin A chain, mutant *Pseudomonas* exotoxins, diphtheria toxoid, streptonigrin, boamycin, saporin, gelonin, and pokeweed antiviral protein. Chemotherapeutics include 5-fluorouracil (5-FU), daunorubicin, cisplatinum, bleomycin, melphalan, taxol, tamoxifen, mitomycin-C, and methotrexate as well as any of the compounds described in U.S. Pat. No. 6,372,719 (the disclosure of which is incorporated herein by reference) as being chemotherapeutic agents. Radionuclides include radiometals. Photodynamic agents include porphyrins and their derivatives. Angiogenesis inhibitors are known in the art and include natural and synthetic biomolecules such as paclitaxel, O-(chloroacetyl-carbomyl) fumagillol ("TNP-470" or "AGM 1470"), thrombospondin-1, thrombospondin-2, angiostatin, human chondrocyte-derived inhibitor of angiogenesis ("hCHIAMP"), cartilage-derived angiogenic inhibitor, platelet factor-4, gro-beta, human interferon-inducible protein 10 ("IP10"), interleukin 12, Ro 318220, tricyclodecan-9-yl xanthate ("D609"), irsogladine, 8,9-dihydroxy-7-methyl-benzo[b]quinolizinium bromide ("GPA 1734"), medroxyprogesterone, a combination of heparin and cortisone, glucosidase inhibitors, genistein, thalidomide, diamino-antraquinone, herbimycin, ursolic acid, and oleanolic acid. Anti-tumor therapy includes the administration of an anti-tumor agent or other therapy, such as radiation treatments, that has been reported as being useful for treating cancer.

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically $C_1$-$C_6$ alkyl groups include, but are not limited to, methyl, ethyl, n-propyl, iso-propyl, butyl, iso-butyl, sec-butyl, tert-butyl, pentyl, hexyl and the like.

The term "$C_2$-$C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n=4-8, represents cyclopropyl, cyclobutyl, cyclopentyl, cyclohexyl, cycloheptyl, and cyclooctyl.

As used herein, the term "optionally substituted" refers to from zero to four substituents, wherein the substituents are each independently selected. Each of the independently selected substituents may be the same or different than other substituents.

As used herein the term "aryl" refers to a mono- or bicyclic carbocyclic ring system having one or two aromatic rings including, but not limited to, phenyl, benzyl, naphthyl, tetrahydronaphthyl, indanyl, indenyl, and the like. Substituted aryl includes aryl compounds having one or two $C_1$-$C_6$ alkyl, halo or amino substituents. The term ($C_5$-$C_8$ alkyl)aryl refers to any aryl group which is attached to the parent moiety via the alkyl group. The term "heterocyclic group" refers to a $C_3$-$C_8$ cycloalkyl group containing from one to three heteroatoms wherein the heteroatoms are selected from the group consisting of oxygen, sulfur, and nitrogen.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like. Any ring structure drawn with one or more bonds extending from the center of the ring is intended to designate a series of compounds that have a bond(s) extending from one of the carbon atoms of the ring to another atom. For example, the structure:

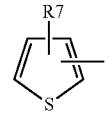

designates a series of compounds including 2-thienyl or 3-thienyl groups that contain an $R_7$ substituent at one of the remaining ring carbon atoms.

The compounds of the present invention contain one or more asymmetric centers in the molecule. In accordance with the present invention a structure that does not designate the stereochemistry is to be understood as embracing all the various optical isomers, as well as racemic mixtures thereof.

The term "pharmaceutically acceptable salt" refers to salts which retain the biological effectiveness and properties of the compounds of the present invention and which are not biologically or otherwise undesirable. In many cases, the compounds of the present invention are capable of forming acid and/or base salts by virtue of the presence of amino and/or carboxyl groups or groups similar thereto.

It is understood to one skilled in the art that "T type calcium channel inhibitors" are also known as "T type calcium channel inhibitors".

DETAILED DESCRIPTION OF THE INVENTION

Changes in the cytosolic concentration of calcium are a critical component of numerous cellular processes. The calcium necessary for these changes comes from the extracellular milieu via influx through calcium channels. Calcium channels are grouped into several families based upon sequence analysis, biophysical characteristics and pharmacological sensitivity. Among these is the T type calcium channel family. These calcium channels have been implicated in regulation of blood pressure, cardiac rhythm, and cellular proliferation. However there has been only one pharmacological agent, mibefradil, that has been proven to be clinically effective because of inhibition of T channel function. Unfortunately, mibefradil was withdrawn from market due to adverse interactions with other drugs leaving this therapeutic approach unavailable.

One embodiment of the present invention is directed to a series of novel synthetic compounds that inhibit calcium entry via T type calcium channels while other members of this series activate calcium entry. Inhibitors of calcium entry will be useful for treating hypertension, cardiac arrhythmia and clinically deleterious cellular proliferation while activators of calcium entry will be useful as a cardiac stimulants and inducers of programmed cell death with the intent of reducing the burden of clinically unwanted cells such as cancer cells. Examples of these compounds are as follows:

Exhibit A

Presence of Oxygen Atom

Series 1

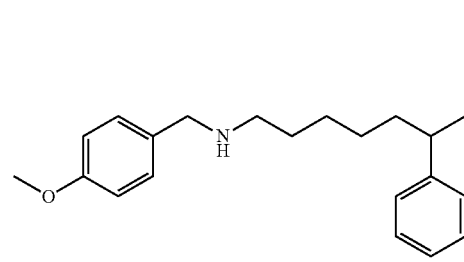

3.1

Series 2

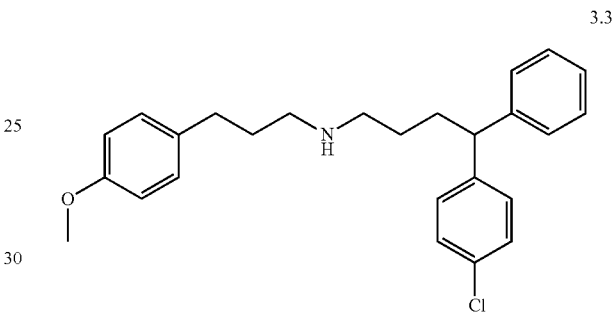

3.2

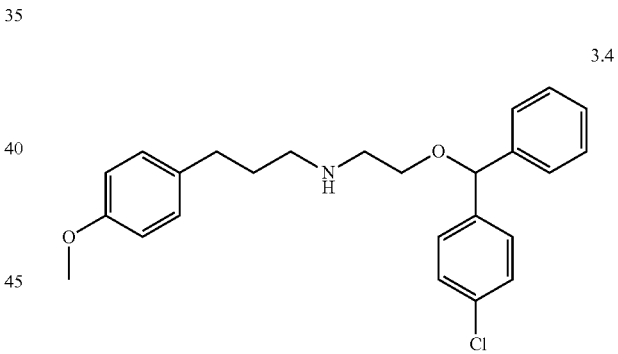

3.3

3.4

TABLE 5.1

|   | Jurkat | | PC3 | | LNCaP | | MDA-435 | | MDA-231 | | MDA-361 | |
|---|---|---|---|---|---|---|---|---|---|---|---|---|
|   | prolif | Ca2+ | prolif | Ca2+ | prolif | Ca2+ | prolif | Ca2+ | prolif | Ca2+ | prolif | Ca2+ |
| Series 1 | | | | | | | | | | | | |
| 3.1 | 4 | 10 | 11 | NE | 35 | 10 | 12 | 25 | 6 | 10 | 8 | 10 |
| 3.2 | 3 | 3 | 9 | 10 | 2 | 5 | 10.5 | 10 | 10 | 8 | 4 | 8 |
| Series 2 | | | | | | | | | | | | |
| 3.3 | 70 | 60 | >100 | NE | 42 | NE | >100 | | >100 | 100 | | |
| 3.4 | 3.7 | 3 | 10 | −15 | 5.5 | 15 | 10 | 15 | 4 | −20 | 4 | 10 |

NE = no effect at the highest concentration of drug tested, all values in micromolar In all Figures, "prolif" indicates the $IC_{50}$ for inhibition of proliferation of the indicated cell lines while "Ca2+" is the $IC_{50}$ for inhibition of calcium entry. As can be seen in this Figure, the presence of an ether linkage has a profound effect of biological activity but only when the amine is proximal to it.

Presence of Nitrogen

Series 1

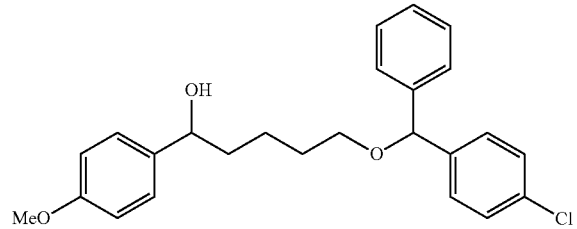
3.5

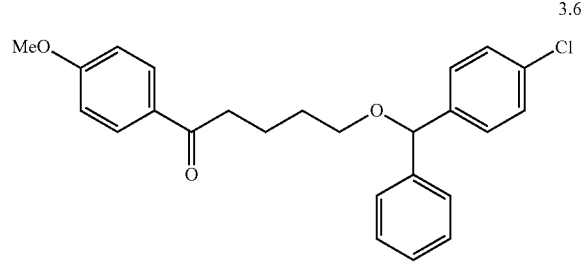
3.6

Series 2

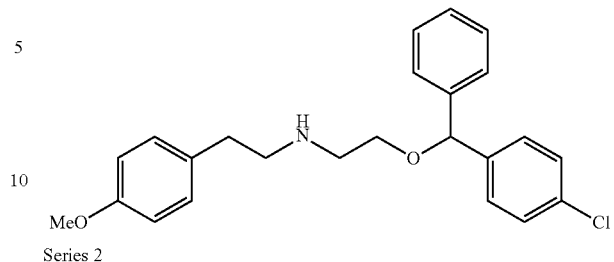
3.8

3.7

3.9

TABLE 5.2

| | Jurkat | | PC3 | | LNCaP | | MDA-435 | | MDA-231 | | MDA-361 | |
|---|---|---|---|---|---|---|---|---|---|---|---|---|
| | prolif | Ca2+ | prolif | Ca2+ | prolif | Ca2+ | prolif | Ca2+ | prolif | Ca2+ | prolif | Ca2+ |
| Series 1 | | | | | | | | | | | | |
| 3.5 | 60 | 7 | 33 | 30 | 25 | 10 | 65 | 10 | 50 | 10 | 45 | 25 |
| 3.6 | >100 | >100 | >100 | NE | −100 | NE | >100 | NE | >100 | NE | >100 | NE |
| 3.8 | 7.5 | 10 | 11.5 | 10 | 3.5 | 10 | 15.7 | 10 | 10.6 | 10 | 7.6 | 20 |
| Series 2 | | | | | | | | | | | | |
| 3.7 | −100 | 10 | NE | NE | −100 | NE | NE | NE | >100 | 60 | >100 | NE |
| 3.9 | 3.5 | 3 | 4 | NE | 1.6 | 3 | 12 | 10 | 11.7 | 10 | 4 | 5 |

NE = no effect at the highest concentration of drug tested, all values in micromolar This Figure demonstrates that nitrogen in the hydrocarbon "tether" is required for biological activity.

Basicity of the Nitrogen

Series 1

3.10

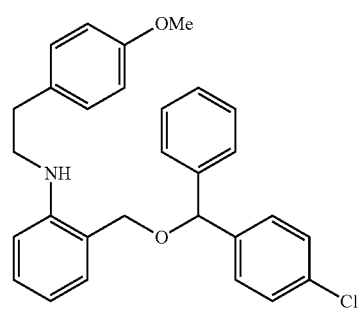

3.11

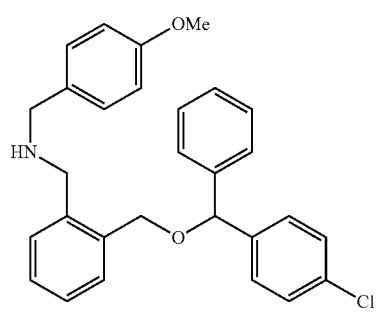

Series 2

3.14

3.15

TABLE 5.3

|  | Jurkat | | PC3 | | LNCaP | | MDA-435 | | MDA-231 | | MDA-361 | |
|---|---|---|---|---|---|---|---|---|---|---|---|---|
|  | prolif | Ca2+ | prolif | Ca2+ | prolif | Ca2+ | prolif | Ca2+ | prolif | Ca2+ | prolif | Ca2+ |
| Series 1 | | | | | | | | | | | | |
| 3.10 | >300 | NE | >1 mM | NE | >1 mM | NE | >1 mM | NE | >1 mM | NE | ~70 | NE |
| 3.11 | 5.4 | 3.3 | 14 | NE | 3.3 | NE | 22 | NE | 11.6 | 20 | 8.5 | 10 |
| Series 2 | | | | | | | | | | | | |
| 3.14 | >100 | 30 | >100 | NE | >100 | 30 | NE | 30 | NE | 30 | NE | 10 |
| 3.15 | 4 | 10 | 11 | NE | 3.5 | 10 | 12 | 25 | 8 | 10 | 8 | 10 |

NE = no effect at the highest concentration of drug tested, all values in micromolar This Figure demonstrates that the basicity of the nitrogen contributes to the biological activity.

Steric Bulk Around the Nitrogen

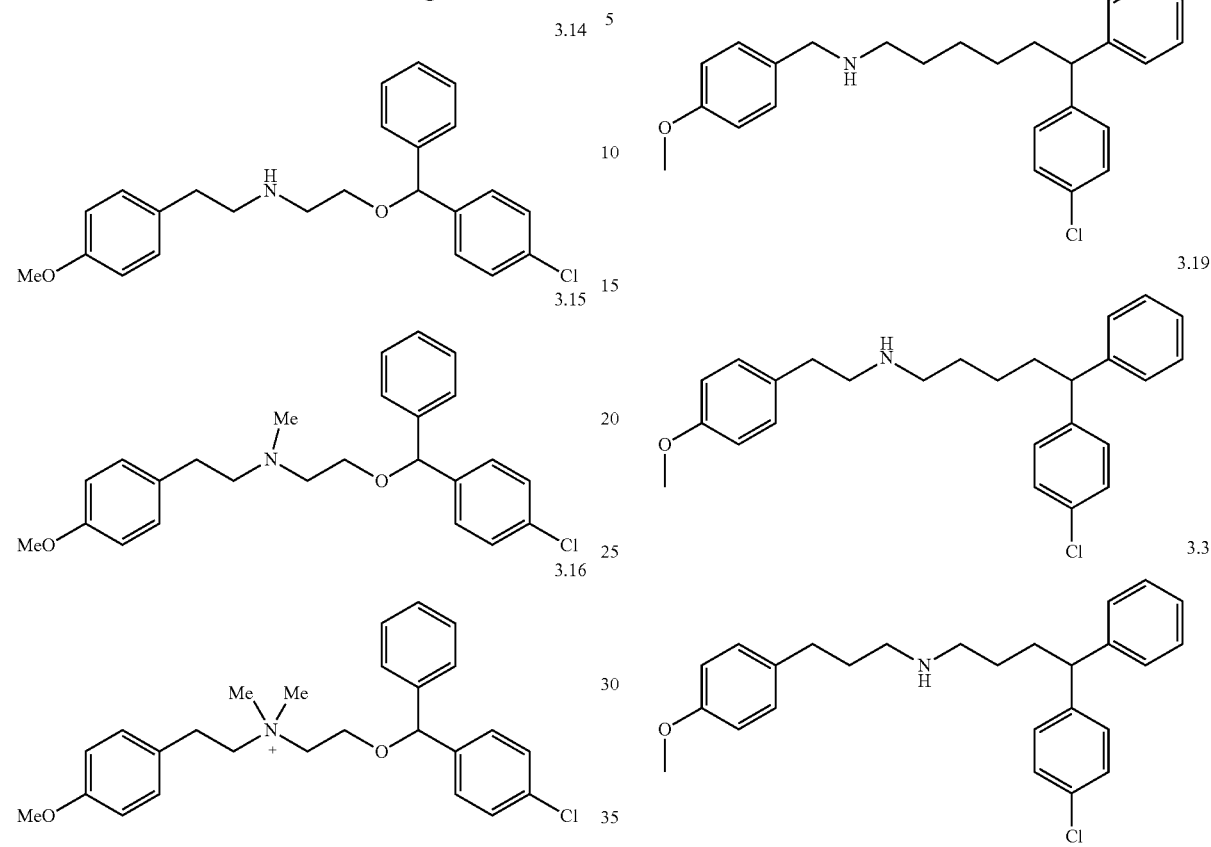

TABLE 5.4

| | | | Increasing steric bulk around the nitrogen → | | | | | | | | |
| | | | ← Increasing biological activity | | | | | | | | |
| Compound | Jurkat prolif | Ca2+ | PC3 prolif | Ca2+ | LNCaP prolif | Ca2+ | MDA-435 prolif | Ca2+ | MDA-231 prolif | Ca2+ | MDA-361 prolif | Ca2+ |
|---|---|---|---|---|---|---|---|---|---|---|---|---|
| 3.14 | 7.6 | 10 | 11.5 | 10 | 35 | 10 | 15.7 | 10 | 106 | 10 | 76 | 20 |
| 3.15 | 12 | 10 | 32 | 20 | 4 | 7 | 27 | 20 | 24 | 10 | 16 | 20 |
| 3.16 | 23 | 30 | 55 | NE | 33 | 10 | 50 | NE | 21 | NE | 8 | NE |

NE = no effect at the highest concentration of drug tested, all values in micromolar
From this Figure, it can be seen that steric bulk around the nitrogen decreases biological activity.

Location of the Nitrogen

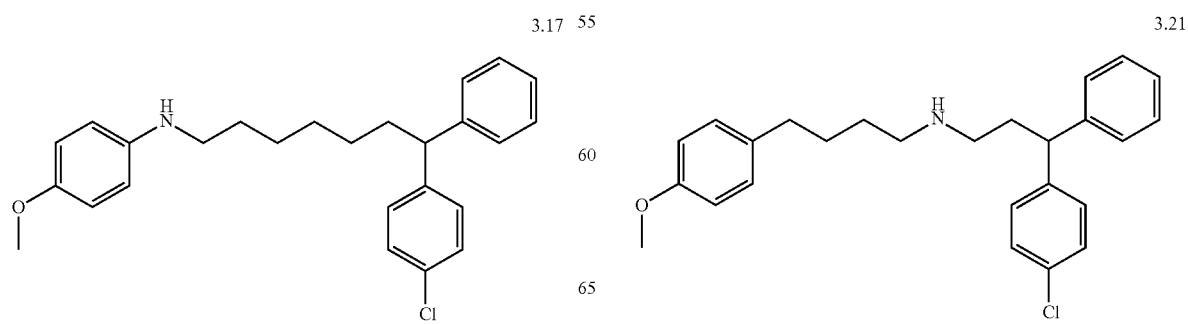

-continued 3.22

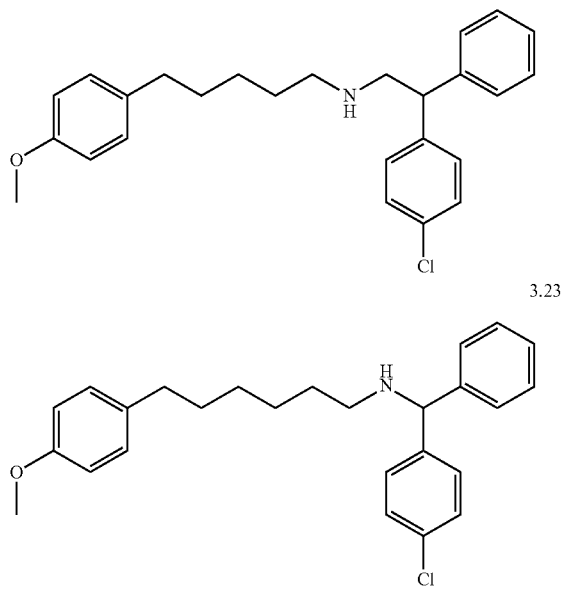

3.23

TABLE 5.5

| Compound | Nitrogen Position | Oxygen Present | Jurkat prolif | Jurkat Ca2+ | PC3 prolif | PC3 Ca2+ | LNCaP prolif | LNCaP Ca2+ | MDA-435 prolif | MDA-435 Ca2+ | MDA-231 prolif | MDA-231 Ca2+ |
|---|---|---|---|---|---|---|---|---|---|---|---|---|
| 3.17 | 1 | no | >100 | 30 | >100 | NE | >100 | 30 | NE | 30 | NE | 30 |
| 3.1 | 2 | no | 4 | 10 | 11 | NE | 3.5 | 10 | 12 | 25 | 8 | 10 |
| 3.19 | 3 | no | 4 | 10 | 10 | NE | 3 | 10 | 11 | 10 | 6 | 10 |
| 3.3 | 4 | no | 70 | 60 | >100 | NE | 42 | NE | >100 | | >100 | 100 |
| 3.21 | 5 | no | 30 | 30 | 11 | 30 | 7 | NE | 9 | | 15 | 30 |
| 3.2 | 6 | no | 13 | 3 | 9 | NE | 9 | NE | 40 | NE | 25 | 10 |
| 3.23 | 7 | no | −30 | NE | >100 | NE | −100 | NE | NE | NE | NE | NE |

NE = no effect at the highest concentration of drug tested, all values in micromolar This Figure shows that biological activity is affected by the position of the nitrogen along the hydrocarbon tether.

In accordance with one embodiment a novel compound that inhibit Ca2+ entry, and thereby proliferation of cancer cells is provided. The compounds have the general structure of Formula (I):

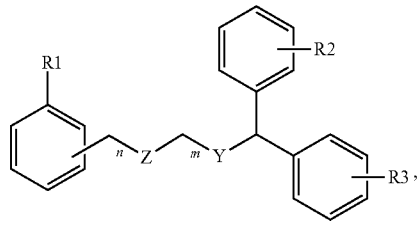

Formula(I)

wherein $R_1$ is $C_1$-$C_4$ alkyl, hydroxy, or $C_1$-$C_4$ alkoxy;

Z is NH, NCH$_3$, O, S, or CH$_2$;

Y is NH, O, or CH$_2$ with the proviso that Y and Z are not the same;

$R_2$ is H, halo, NH$_2$, $C_1$-$C_4$ alkyl, hydroxy, or $C_1$-$C_4$ alkoxy;

m and n are independently selected from integers ranging from 1-5 with the proviso that m+n=an integer ranging from 2-9; and $R_3$ is H, halo, NH$_2$, $C_1$-$C_4$ alkyl, hydroxy, or $C_1$-$C_4$ alkoxy;

or a pharmaceutically acceptable salt thereof.

Preferably, $R_1$ is hydroxy or $C_1$-$C_4$ alkoxy; Z is N or O; $R_2$ is H, halo, NH$_2$ or hydroxy; and $R_3$ is H.

The novel compounds of the present invention can be combined with standard pharmaceutically acceptable carriers or other known anti-tumor and chemotherapeutic agents.

Materials and Methods

Synthesis of TH-1177:

TH-1177 was synthesized in three simple steps as described (Haverstick, D. M., Heady, T. N., Macdonald, T. L., and Gray, L. S. 2000. Inhibition of human prostate cancer proliferation in vitro and in a mouse model by a compound synthesized to block Ca$^{2+}$ entry. Cancer Res 60:1002-1008). L-Proline methyl ester was coupled with 4-methoxyphenylacetic acid using benzotriazol-1-yl-oxytripyrrolidinephosphonium to generate methyl 1-[2-(4 methoxyphenyl)acetyl] pyrrolidine-2-carboxylate, a yellowish oil. The resulting amide was subsequently reduced to the amino alcohol with LiAIH4 and AICI3 in tetrahydrofuran. The resulting colorless oil was coupled with 4-chlorobenzhydrol under Williamson conditions with catalytic p-toluenesulfonic acid in refluxing toluene. The final brownish oil was isolated by column chromatography, and its structure was confirmed by nuclear magnetic resonance and mass spectrometry. TH-1177 was dissolved in DMSO for use.

Cell Lines and Maintenance:

Cancer cell lines were obtained from the American Type Culture Collection (Manassas, Va.). Cell lines were maintained in RPMI1640 supplemented with glutamine and 5% fetal bovine serum containing SerXtend (Irvine Scientific) when appropriate insulin, as directed by the ATCC. The fetal bovine serum used for culture was heat-inactivated by maintaining the serum at 56° C. for 1 h. Cell lines used were a T cellleukemia (Jurkat), prostate cancer (PC3, DU145, LNCaP), breast cancer (MDA468, MDA361, MCF7), pancreatic cancer (MIA PaCa2), liver cancer (Hep G2), lung cancer (A549, NCI H460), colon cancer (HT29, HCT 116), and ovarian cancer (SK-OV-3).

Measurement of the [Ca2+]i Concentration:

Cells were incubated in growth media containing 1 uM of the acetoxy-methyl ester of the Ca2+-sensitive fluorescent dye indo-1 (indo-1/AM; Molecular Probes, Eugene, Oreg.) for 1 h at 37° C. Cells were washed three times in buffer A [10 mM HEPES (pH 7.4), 1 mM MgCl$_2$, 3 mM KCl, 1 mM CaCl$_2$, 140 mM NaCl, 0.1% glucose, and 1% fetal bovine serum] and suspended to a final concentration of 10$^6$ cells/ml. Before stimulation, cells were warmed to 37° C.

Changes in [Ca2+]i were monitored in an SLM 8100C spectrofluorometer (SLM/Aminco; Urbana, Ill.) using previously published methods (Densmore, J. J., Haverstick, D. M., Szabo, G., and Gray, L. S. 1996. A voltage operable current is involved in activation-induced $Ca^{2+}$ entry in human lymphocytes whereas $I_{CRAC}$ has no apparent role. *Am. J. Physiol.* 271:C1494-C1503; Haverstick, D. M., Densmore, J. J., and Gray, L. S. 1998. Calmodulin regulation of $Ca^{2+}$ entry in Jurkat T cells. *Cell Calcium* 23:361-368).

Measurement of Cellular Proliferation:

LNCaP cells at $2.5\times10^4$ cells/well or PC-3 cells at $5\times10^4$ cells/well, both in a final volume of 100 I.JI, were plated in triplicate in standard flat-bottomed 96-well tissue culture plates in the presence of drug or vehicle (DMSO). Unless otherwise indicated, cells were grown for 48 h at 37° C. in a $CO_2$ incubator. Relative cell growth was determined with the CellTiter 96 aqueous cell proliferation assay (Promega, Madison, Wis.) as described by the manufacturer using an automated plate reader. Results were calculated in a blinded fashion and are the means of triplicate determinations.

Results

Figure 1B:
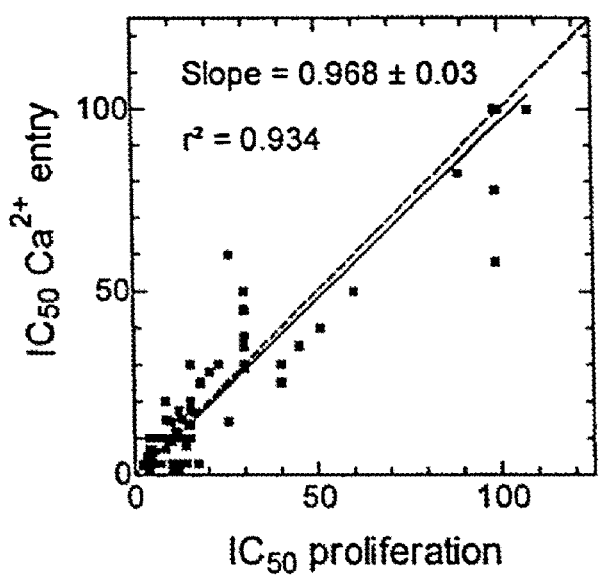

Construction of a Novel Chemical Library:

Extracellular Ni2+ blocks the Ca2+ entry pathway in electrically non-excitable cells (Merritt, J. E., Jacob, R., and Hallam, T. J. 1989. Use of manganese to discriminate between calcium influx and mobilization from internal stores in stimulated human neutrophils. *J. Biol. Chem.* 264:1522-1527; Jones, G. R. N. 1985. Cancer therapy: Phenothiazines in an unexpected role. *Tumori* 71:563-569) as well as the current through T type Ca2+ channels (Lee, J.-H., Gomora, J. C., Cribbs, L. L., and Perez-Reyes, E. 2000. Nickel block of three cloned T-type Ca channels: low concentrations selectively block α1H. *Biophys. J.* 77:3042). We made use of these facts and conducted a search of the Medline database for compounds that block Ca2+ entry in any system that was also sensitive to inhibition of Ca2+ entry by Ni2+. The identified compounds were then used as the basis for a reiterated search. This strategy was continued until the only citations returned were those that had been retrieved already indicating that the database had been saturated. These agents, some of which are listed in Table 1, were tested for the ability to block proliferation of and Ca2+ entry into the Jurkat human cancer cell line. These compounds were tested in various cancer cell lines (Materials and Methods) with results similar to those obtained with the Jurkat cell line (data not shown). The correlation between these two inhibitory activities in the Jurkat cell line, expressed as ICso's, is shown in FIG. 1, panel A. The resulting structure-activity relationship (SAR) was used as a guide to synthesize novel chemical agents. These novel compounds exhibited enhanced inhibition of Ca2+ into and proliferation (Table 2). The slope of the regression line between the ability of the novel compounds to inhibit proliferation and block Ca2+ entry was 0.97 or very close to unity with an $r^2$ value of 0.93 (FIG. 1, panel B) compared to a slope of 0.73 ($r^2$=0.79) for the known agents (FIG. 1, panel A). Because Ca2+ entry is required for proliferation (Berridge, M. J., Lipp, P., and Bootman, M. D. 2000. The versatility and universality of calcium signalling. *Nat. Rev. Mal Cell Biol.* 1:11-21), the slope of 0.97 should most appropriately be interpreted in a Bayesian fashion. This Bayesian analysis suggests that all of the effect of these compounds on proliferation is mediated through inhibition of Ca2+ entry.

Figure 2A:
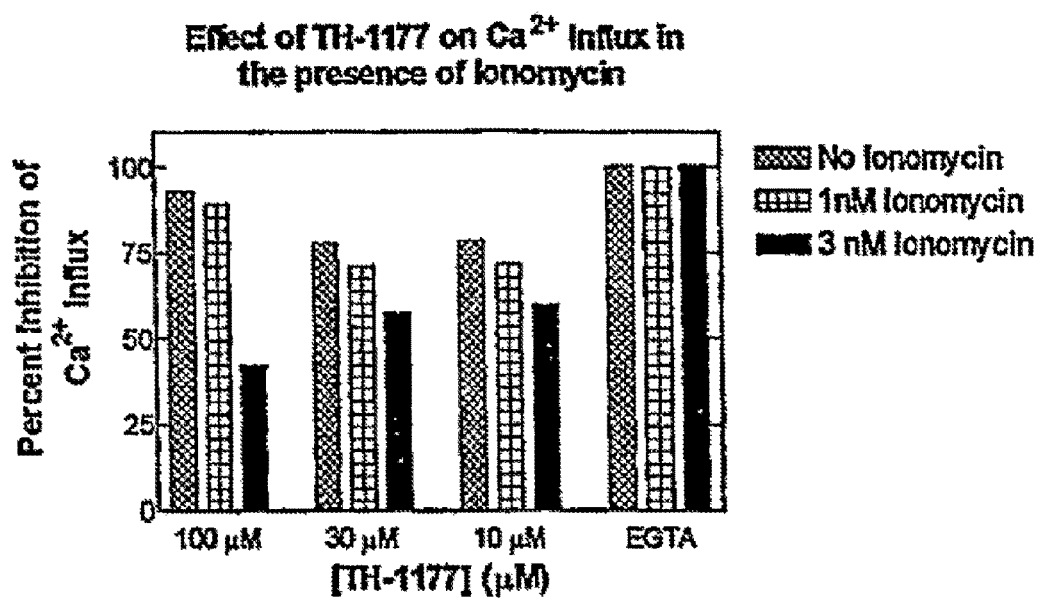
FIG. 2. The Ca2+ ionophore ionomycin overcomes the inhibition of Ca2+ entry into and proliferation of Jurkat cells produced by TH-1177. Panel A. Ca2+ entry into Jurkat cells was determined as described in Materials and Methods. Ionomycin at the indicated concentrations was added 30 s and the mitogenic monoclonal antibody OKT3 was added at a concentration of 1 ug/ml at 60 s. Either EGTA at 2.5 mM or TH-1177 at the indicated concentrations was added at 150 s. The percentage inhibition was determined as described in Material and Methods. Panel B. Jurkat cells were grown for 48 hrs in the presence (open symbols) or absence (closed symbols) of 30 nM ionomycin and the indicated concentrations of TH-1177. Percent control growth was determined as described in Materials and Methods.
Figure 2B:
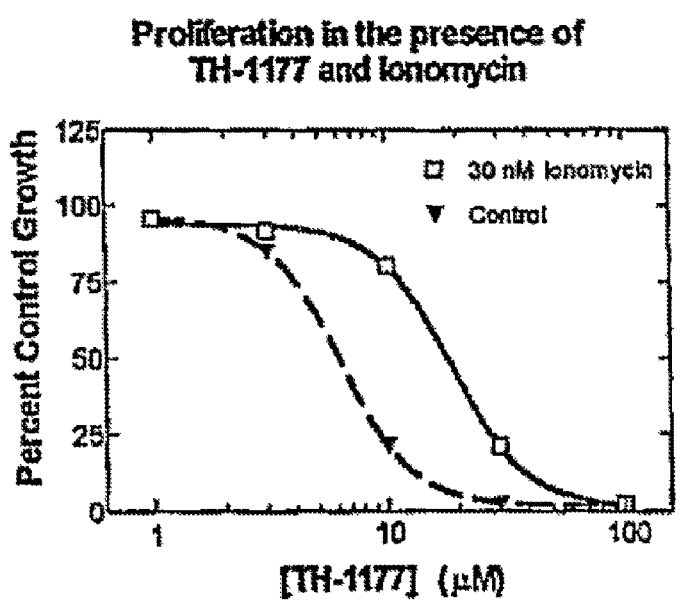
Figure 3:
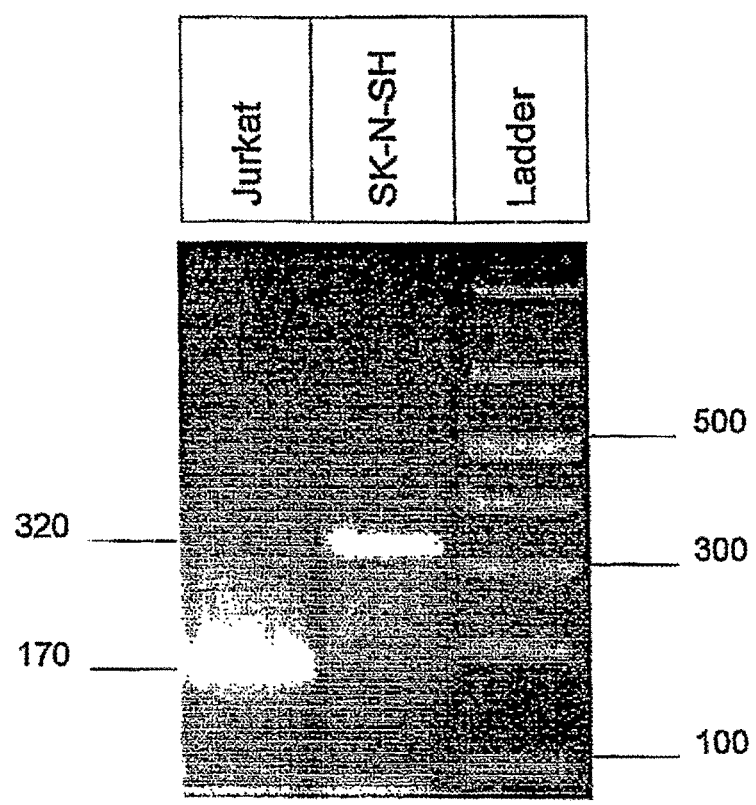
FIG. 3. Amplicons of two sizes were identified in Jurkat and SK-N-SF cancer cell lines using α1H Ca2+ channel specific PCR primers. Messenger RNA was extracted and amplified as described in Materials and Methods using the primers described previously (Mariot, P., Vanoverberghe, K., Lalevee, N., Rossier, M. F., and Prevarskaya, N. 2002. Overexpression of an alpha 1H (Cav3.2) T-type calcium channel during neuroendocrine differentiation of human prostate cancer cells. *J Biol. Chem* 277:10824-10833). The resulting products were isolated by gel electrophoresis and visualized by ethidium bromide staining and visualized by UV illumination.
Figure 5:
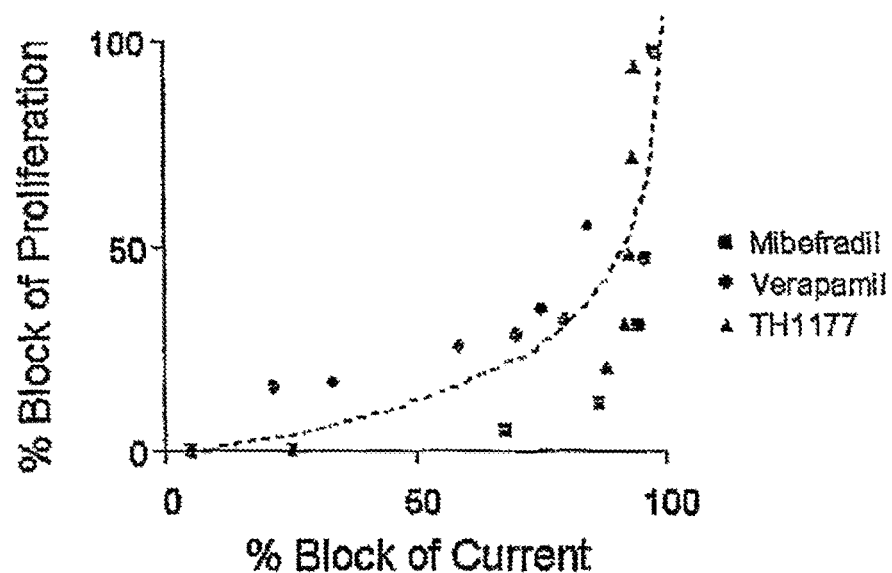
FIG. 5. Blockade of the α1H Ca2+ current by the known T type Ca2+ channel mibefradil or TH-1177 inhibits proliferation of stably transfected HEK293 cells. HEK293 cells were stably transfected the α1H gene as described in Materials and Methods. Proliferation and the Ca2+ current were determined as described in Materials and Methods.
Figure 6B:
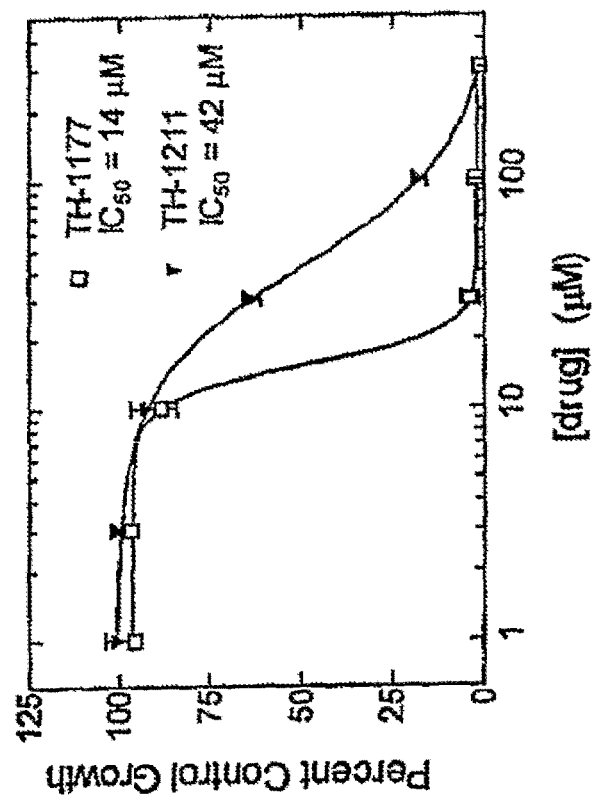
FIG. 6. TH-1177 and TH-1211 are stereoisomers about one of two chiral centers and have different potencies at inhibiting the proliferation of PC3 prostate cancer cells. Panel A: The structures of TH-1177 and TH-1211 were determined as described in Materials and Methods. The diastereomers are racemic at the benzhydrol center (solid arrows) and enantiomeric at the proline center (open arrows) with TH-1177 having the S configuration and TH-1211 having the R. Panel B: The proliferation of PC3 human prostate cancer cells was determined as described in Materials and Methods. The IC50 for TH-1177 was 14 uM (open boxes) and for TH-1211 was 42 uM (inverted triangles).
Figure 6A:
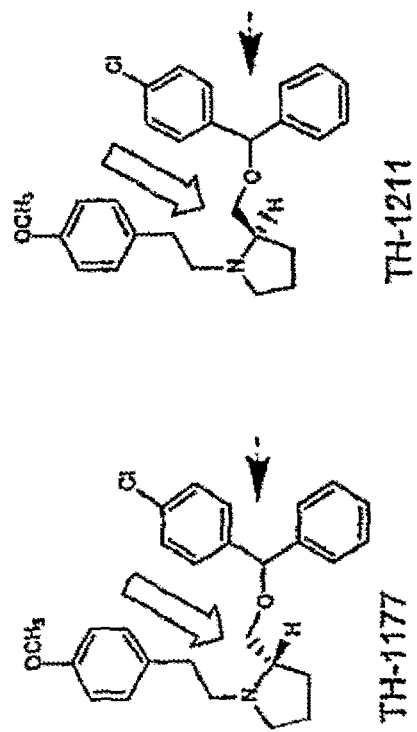
Figure 7B:
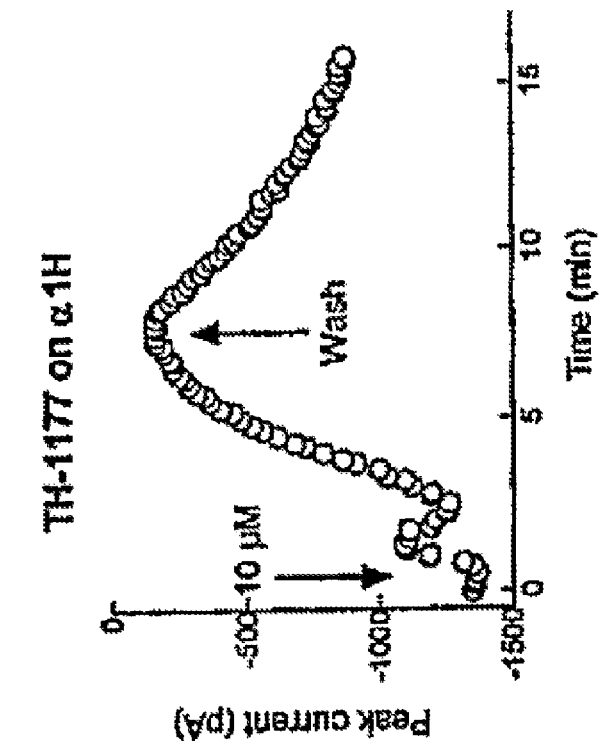
FIG. 7. TH-1177 and TH-1211 have different potencies at inhibiting the Ca2+ current through transfected α1H channels. The current carried by transfected α1H Ca2+ channels was determined as described in Materials and Methods. The concentration response for TH-1177 and TH-1211 is shown in FIG. 7D. The IC50 for TH-1177 was 0.8 uM and for TH-1211 was 7 uM.
Figure 7A:
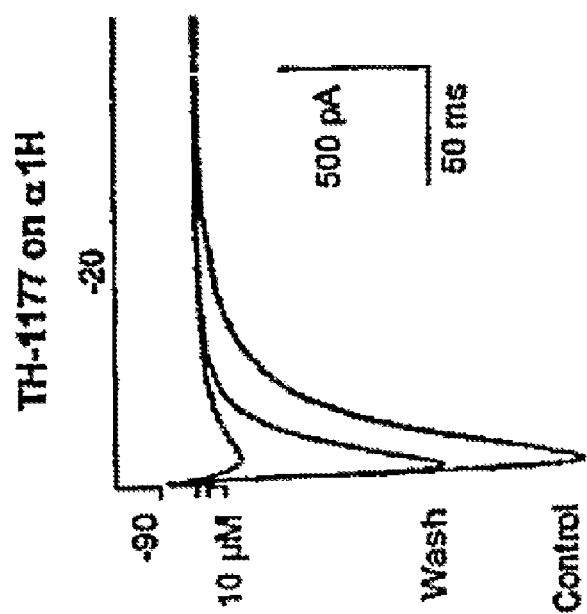

The Ca2+ ionophore ionomycin partially overcomes the effects of TH-1177. We have used one of our compounds, TH-1177, as the prototype for the others (Haverstick, D. M., Heady, T. N., Macdonald, T. L., and Gray, L. S. 2000. Inhibition of human prostate cancer proliferation in vitro and in a mouse model by a compound synthesized to block $Ca^{2+}$ entry. *Cancer Res* 60:1002-1008). If TH-1177 is acting via inhibition of Ca2+ entry, its effects should be at least partially reversed by direct elevation of [Ca2+]i using a Ca2+ ionophore. As shown in FIG. 2, panel A, ionomycin overcame inhibition of Ca2+ entry by TH-1177 in a concentration dependent manner although there was no effect on proliferation of 30 nM ionomycin alone. Ionomycin also reduced the ability of TH-1177 to inhibit proliferation (FIG. 2, panel B) increasing the IC50 of TH-1177 from 4.6 uM in the presence of 30 uM ionomycin to 17.8 uM in its absence. This suggests that TH-1177 is acting to inhibit proliferation by inhibition of Ca2+ entry and is in accord with the relationship between Ca2+ entry and proliferation shown in FIG. 1.

Cancer cell lines sensitive to our agents express message for the α1H Ca2+ channel or its δ 25 splice variant.

We have presented data previously suggesting that a member or members of the T type Ca2+ channel family have a role in mediating Ca2+ entry in electrically excitable cells (Densmore, J. J., Haverstick, D. M., Szabo, G., and Gray, L. S. 1996. A voltage operable current is involved in activation-induced $Ca^{2+}$ entry in human lymphocytes whereas $I_{CRAC}$ has no apparent role. *Am. J. Physiol.* 271:C1494-C1503; Densmore, J. J., Szabo, G., and Gray, L. S. 1992. A voltage-gated calcium channel is linked to the antigen receptor in Jurkat T lymphocytes. *FEBS Lett.* 312: 161-164; Haverstick, D. M. and Gray, L. S. Increased intracellular $Ca^{2+}$ induces $Ca^{2+}$ influx in human T lymphocytes. Molecular Biology of the Cell 4, 173-184. 1993; Haverstick, D. M., Densmore, J. J., and Gray, L. S. 1998. Calmodulin regulation of $Ca^{2+}$ entry in Jurkat T cells. *Cell Calcium* 23:361-368). It has been shown recently that a prostate cancer line expresses the α1H isoform of T type Ca2+ channels at levels that vary with differentiation status (Mariot, P., Vanoverberghe, K., Lalevee, N., Rossier, M. F., and Prevarskaya, N. 2002. Overexpression of an alpha 1H (Cav3.2) T-type calcium channel during neuroendocrine differentiation of human prostate cancer cells. *J Biol. Chem* 277:10824-10833). Using the same primers, reported in that study, the value for TH-1211 is 24 uM. Thus, when measured by Ca2+ selective fluorescent dyes, Ca2+ entry was similarly sensitive to TH-1177 and TH-1211 as was the Ca2+ current mediated by α1H. As importantly, each of these measures of Ca2+ influx showed the same relative difference in sensitivity to the stereoisomers.

This shows the pharmacological correspondence between capacitative Ca2+ entry when measured by fluorescence and Ca2+ entry mediated by α1H when measured by electrophysioioglcai methods.

Discussion

Recently, several channels have been suggested as candidates for mediating Ca2+ entry in electrically non-excitable cells. A common feature of these proposed Ca2+ entry channels is that they are not voltage gated. This reflects the prevalent assumption that the Ca2+ entry pathways in electrically excitable and non-excitable cells are categorically distinct. It is extremely difficult, however, to understand why such an assumption is necessary particularly in view of the inherently non-categorical nature of biological systems. In addition, these voltage insensitive Ca2+ channels do not fulfill completely the biophysical criteria for the capacitative Ca2+ entry pathway in electrically non-excitable cells (Haverstick, D. M. and Gray, L. S. Increased intracellular $Ca^{2+}$ induces Ca$^{2+}$ influx in human T lymphocytes. Molecular Biology of the Cell 4, 173-184. 1993).

This uncertainty about the nature of Ca2+ entry in electrically non-excitable cells may be the result of a number of technical factors in addition to the constraints imposed by unnecessary assumption. While several of the proposed candidates for mediation of Ca2+ entry in electrically non-excitable cells have been characterized at the molecular level (Putney, J. W., Jr. and McKay, R. R. 1999. Capacitative calcium entry channels. *Bioessays* 21:38-46), a commonly accepted Candidate, $I_{CRAC}$ (Clapham, D. E. 2002. Sorting out MIC, TRP, and CRAC Ion Channels. *J. Gen. Physiol* 120:217-220; Cahalan, M. D., Wulff, H., and Chandy, K. G. 2001. Molecular properties and physiological roles of ion channels in the immune system. *J Clin Immunol.* 21:235-252), has not. It is also difficult to tie the function of these channels to inhibition of proliferation of cancer cell lines because of the paucity of specific Ca2+ entry inhibitors for electrically non-excitable cells. There is as well the unavoidable disjunction between Ca2+ entry as measured by Ca2+ selective fluorescent dyes and electrophysiological methods: The patch-ctamp technique is extraordinarily powerful for examining the biophysical details of the function of an ion channel (Neher, E. and Sakmann, B. 1992. The patch clamp technique. *Scientific American March:*44-51), however the level of membrane control it both achieves and requires makes it less suited to identifying a channel's physiological role. Fluorescence techniques are very limited in obtaining biophysical detail but better able to study physiological roles. This disconnection makes it difficult to determine if the effects of physiologically relevant stimuli, as determined by fluorescence measurements, are reproduced at the electrophysiological level.

We have suggested that the mechanism of Ca2+ entry in electrically non-excitable cells involves a Ca2+ channel sharing characteristics with the T type family of voltage gated Ca2+ channels (Densmore, J. J., Haverstick, D. M., Szabo, G., and Gray, L. S. 1996. A voltage operable current is involved in activation-induced Ca$^{2+}$ entry in human lymphocytes whereas $I_{CRAC}$ has no apparent role. *Am. J. Physiol.* 271:C1494-C1503; Densmore, J. J., Szabo, G., and Gray, L. S. 1992. A voltage-gated calcium channel is linked to the antigen receptor in Jurkat T lymphocytes. *FEBS Lett.* 312:161-164; Haverstick, D. M. and Gray, L. S. Increased intracellular Ca$^2$; induces Ca$^{2+}$ influx in human T lymphocytes. Molecular Biology of the Cell 4, 173-184. 1993; Haverstick, D. M., Densmore, J. J., and Gray, L. S. 1998. Calmodulin regulation of Ca$^{2+}$ entry in Jurkat T cells. *Cell Calcium* 23:361-368). It could be argued that it is difficult to envision a physiologic role for voltage gated Ca2+ channels in cells that do not have action potentials. This argument is, however, based upon the assumption that a voltage gated Ca2+ channel can be only be activated by an action potential. Such an assumption is false a priori because the means by which a protein can be regulated by imposed experimental conditions is not necessarily identical with, or even similar to, the mechanism by which it is controlled physiologically. Although secondary to regulation by membrane potential, the known biochemical regulation of voltage gated Ca2+ channels in a variety of systems also suggests that the categorical distinction between electrical and biochemical regulation of Ca2+ channels may be simplistic.

The data presented here strongly suggest the possibility that the α1H isoform of nominally voltage gated T type Ca2+ channels or its δ 25 splice variant has a role in Ca2+ entry into and proliferation of electrically non-excitable cancer cells. Our data show that novel compounds can be created based upon an structure-activity relationship generated from compounds that are known to inhibit Ca2+ entry in systems that are also sensitive to inhibition by Ni2+. These novel compounds also inhibit proliferation of several cancer cell lines via blockade of Ca2+ entry. The cell lines that are sensitive to our agents express message for α1H Ca2+ channels, its δ 25 splice variant, or both. These compounds also inhibit the Ca2+ current mediated by α1H Ca2+ channels and slow the proliferation of HEK293 cells stably transfected with the α1H Ca2+ channel isoform. TH-1177 and TH-1211 stereoselectively inhibit Ca2+ entry into and proliferation of cancer cell lines and show the same-stereosetectivity and potency in blocking canonical α1H. These data strongly suggest that the α1H Ca2+ channel and its δ 25 splice variant participate in Ca2+ entry in the cancer cell lines tested in these studies.

Linking biophysical analysis of Ca2+ channel function to a physiological function such as proliferation can pose challenges. We have demonstrated that our compounds block a heterologously expressed Ca2+ channel and that only those cancer cell lines with message for that channel, or its splice variant, are sensitive to inhibition by the same agents. Furthermore. TH-1177 is more potent at inhibiting Ca2+ entry via expressed α1H as measured by biophysical techniques than the stereoisomer of it, TH-1211. TH-1177 and TH-1211 also show the same rank order of potency at inhibiting proliferation and Ca2+ entry in cancer cell lines when these are assayed by more commonly used biochemical methods. The absolute potencies of the agents as measured by IC50 values are strikingly similar whether measured by biophysical or biochemical methods. Thus, the results from a combination of experimental approaches were synthesized into a picture of the likely mechanism of Ca+ entry in some cancer cells.

Expression of the α1H Ca2+ channel has been demonstrated in LNCaP cells and the expression level correlates with differentiation state (Mariot, P., Vanoverberghe, K., Lalevee, N., Rossier, M. F., and Prevarskaya, N. 2002. Overexpression of an alpha 1H (Cav3.2) T-type calcium channel during neuroendocrine differentiation of human prostate cancer cells. *J Biol. Chem* 277:10824-10833). Although the sequence of the δ 25 splice variant has been deposited in GenBank (accession number AF223563), its function has not been described to our knowledge. However, both are members of the T type Ca2+ channel family by sequence homology and have been assigned to the Hs. 122359 UniGene cluster within the NCBI database. The physiological roles of T type Ca2+ channels are not wholly clear at present although they may playa role as pacemakers in the heart and central nervous system (Chemin, J., Monteil, A., Perez-Reyes, E., Bourinet, E., Nargeot, J., and Lory, P. 2002. Specific contribution of human T-type calcium channel isotypes ($α_{1G}$, $α_{1H}$ and $α_{1I}$) to neuronal excitability. *J. Physiol. (Lond.)* 540:3-14; McDonald, T. F., Pelzer, S., Trautwein, W., and Pelzer, D. J. 1994. Regulation and modulation of calcium channels in cardiac, skeletal, and smooth muscle cells. *Physiol Rev* 74:365-507). The expression of these Ca2+ channels also appears to be developmentally regulated (Brooks, G., Harper, J. V., Bates, S. E., Haworth, R. S., Cribbs, L. L., Perez-Reyes, E., and Shattock, M. J. 1999. Over expression of the voltage-gated T-type calcium channel induces vascular smooth muscle cell proliferation. *Circulation* 100:1-209(Abstr.); Clozel, J. P., Ertel, E. A., and Ertel, S. I. 1999. Voltage-gated T-type Ca$^{2+}$ channels and heart failure. *Proc. Assoc. Am Physicians* 111:429-437; Harper, J. V., McLatchie, L., Perez-Reyes, E., Cribbs, L. L., Shattock, M. J., and Brooks, G. 2000. T-type calcium channel expression is necessary for G1-S progression in vascular smooth muscle. *Circulation* 102:II-48 (Abstr.); Monteil, A., Chemin, J., Bourinet, E., Mennessier, G., Lory, P., and Nargeot, J. 2000. Molecular and functional properties of the human $\alpha_{1G}$ subunit that forms T-type calcium channels. *J Biol. Chem.* 275:6090-6100) and the data reported here suggest that both canonical α1H and its δ 25 splice variant are responsible for the Ca2+ entry required for proliferation of some cancer cell lines. These data are also consistent with the idea that the so-called voltage gated C12+ channels are likely to have a physiologically role in cell types conventionally categorized as electrically non-excitable.

Our novel synthetic compounds may have clinical utility because treatment of mice bearing xenografted human PC3 prostate cancer cells with TH-1177 significantly extended the lifespan of them (Haverstick, D. M., Heady, T. N., Macdonald, T. L., and Gray, L. S. 2000. Inhibition of human prostate cancer proliferation in vitro and in a mouse model by a compound synthesized to block $Ca^{2+}$ entry. *Cancer Res* 60:1002-1008). Thus, it is possible that Ca2+ channel inhibitors will ultimately provide clinicians with an addition to their armamentarium for the treatment of cancer. The observations presented here, as well as those presented previously (Haverstick, D. M., Heady, T. N., Macdonald, T. L., and Gray, L. S. 2000. Inhibition of human prostate cancer proliferation in vitro and in a mouse model by a compound synthesized to block $Ca^{2+}$ entry. *Cancer Res* 60:1002-1008), lay the groundwork for further developments in this area.

What is claimed is:

1. A method for treating a disease or condition selected from the group consisting of hypertension and cardiac arrhythmia in a mammal in need of such treatment comprising administering to the mammal a therapeutically effective amount of a compound or a pharmaceutically acceptable salt thereof, wherein the compound has a structure represented by Formula (1):

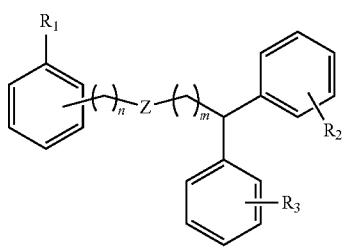

Formula (I)

wherein $R_1$ is $C_1$-$C_4$ alkyl, hydroxy, or $C_1$-$C_4$ alkoxy;

Z is NH, O, S, or $CH_2$;

$R_2$ is H, halo, $NH_2$, $C_1$-$C_4$ alkyl, hydroxy, or $C_1$-$C_4$ alkoxy;

m and n are independently selected from integers ranging from 1-5 with the proviso that m+n=an integer ranging from 4-9; and $R_3$ is chloro or $C_1$-$C_4$ alkoxy.

2. The method according to claim 1, wherein $R_1$ is hydroxy or $C_1$-$C_4$ alkoxy; Z is NH or O; and $R_2$ is H, halo, $NH_2$ or hydroxy.

3. A method for treating a disease or condition selected from the group consisting of unstable angina, hypertension, epilepsy, neuropathic pain, petit mal seizure, absence seizure, age related, macular degeneration and cancer in a mammal in need of such treatment comprising administering to the mammal a therapeutically effective amount of a T type calcium channel inhibitor or a pharmaceutically acceptable salt of said inhibitor, wherein the inhibitor is selected from the group consisting of the following compounds:

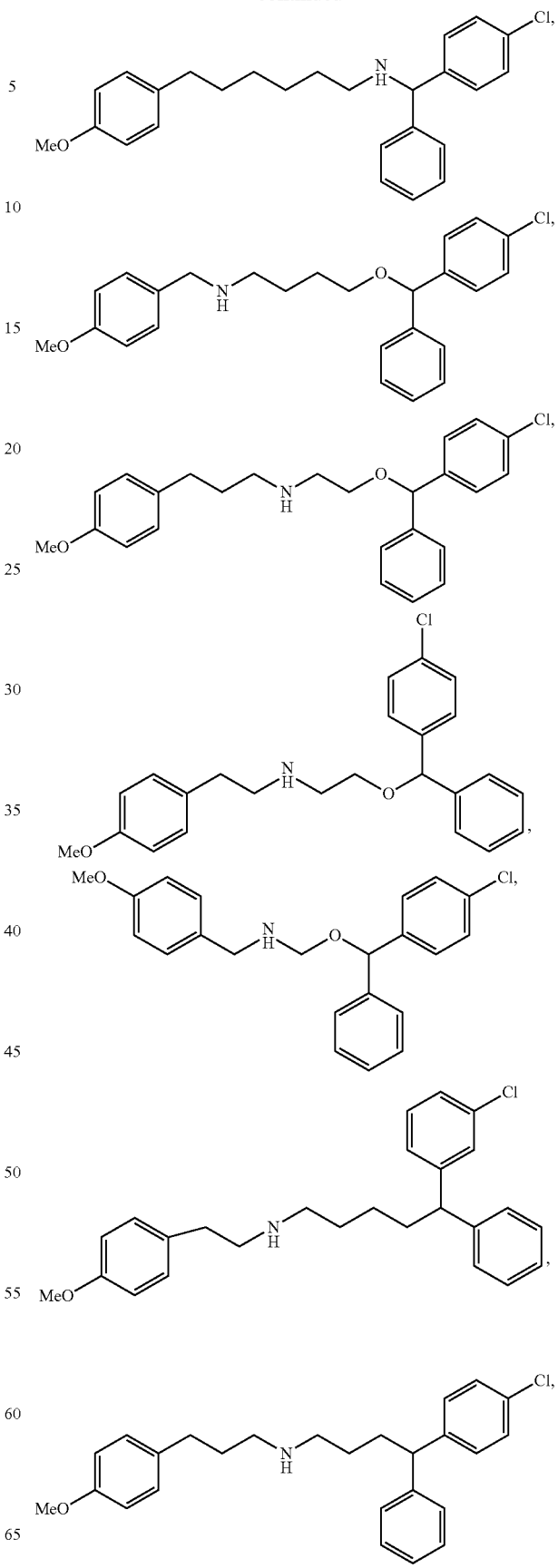

-continued
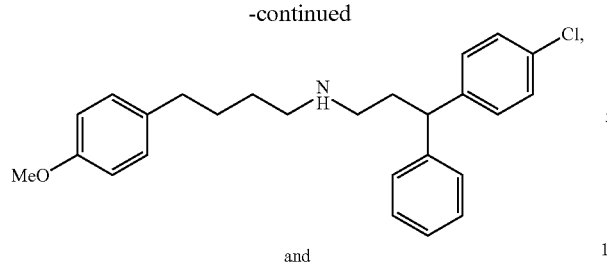
and
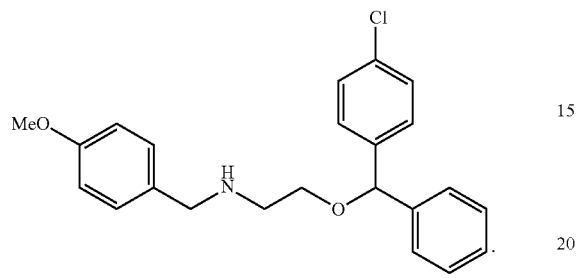
* * * * *